United States Patent [19]

Yoshimoto et al.

[11] Patent Number: 4,619,689
[45] Date of Patent: Oct. 28, 1986

[54] DIPHENYL ETHER DERIVATIVES AND HERBICIDES CONTAINING SAME

[75] Inventors: Takeo Yoshimoto; Akira Hosono; Joh Miki; Yasunobu Funakoshi; Takashi Fujita; Yoshikata Hojo, all of Kanagawa, Japan

[73] Assignee: Mitsui Toatsu Chemicals, Inc., Tokyo, Japan

[21] Appl. No.: 660,579

[22] Filed: Oct. 12, 1984

Related U.S. Application Data

[60] Division of Ser. No. 287,654, Jul. 28, 1981, Pat. No. 4,515,628, which is a continuation of Ser. No. 91,858, Nov. 6, 1979, abandoned.

[30] Foreign Application Priority Data

Nov. 8, 1978 [JP] Japan .................................. 53-136769

[51] Int. Cl.⁴ ...................... A01N 47/28; A01N 37/18; C07C 133/02; C07C 109/10
[52] U.S. Cl. ........................................ 71/119; 71/118; 71/120; 71/88; 71/94; 71/95; 71/96; 71/98; 71/99; 71/87; 71/103; 71/111; 71/121; 564/34; 564/149
[58] Field of Search .................. 71/118, 119, 120; 564/34, 149

[56] References Cited

U.S. PATENT DOCUMENTS

| | | | |
|---|---|---|---|
| 2,763,539 | 9/1956 | McQueen | 71/121 |
| 3,318,680 | 5/1967 | Levitt | 71/120 |
| 3,769,341 | 10/1973 | Alt | 564/34 |
| 3,867,452 | 2/1975 | Wilcox | 71/121 |
| 4,138,244 | 2/1979 | Hunter et al. | 71/121 |

*Primary Examiner*—Catherine L. Mills
*Attorney, Agent, or Firm*—Sughrue, Mion, Zinn, Macpeak, and Seas

[57] ABSTRACT

Novel diphenyl ether hydrazine derivatives, particularly 2-nitro-5 (nucleus-substituted phenoxy) phenylhydrazine derivatives are provided. They are useful as a selective herbicide having a high herbicidal activity and residual efficacy.

8 Claims, No Drawings

DIPHENYL ETHER DERIVATIVES AND HERBICIDES CONTAINING SAME

This application is a divisional application of Ser. No. 287,654, filed July 28, 1981, U.S. Pat. No. 4,515,628, in turn a continuation application of Ser. No. 91,858, filed Nov. 6, 1979, now abandoned.

BACKGROUND OF THE INVENTION

The present invention relates to novel diphenyl ether compounds and novel herbicides containing at least one of the compounds as an active ingredient.

A number of diphenyl ether compounds have heretofore been studied for their practical use as herbicides, but these compounds are, in many cases, much different in the herbicidal activity, the developing manner, the selectivity, the durability of efficacy, etc., depending on slight differences in the chemical structures such as the kind, number and position of their substituents, and it is very difficult to anticipate the herbicidal activity of compounds from the similarity of the chemical structures of compounds.

As disclosed in e.g. U.S. Pat. No. 3,316,080 and Japanese Patent Publication No. 9898/1963, it is well-known that some of diphenyl ether compounds have superior herbicidal activities. For example, 2,4,6-trichloro-4'-nitrodiphenyl ether and 2,4-dichloro-3'-methoxy-4'-nitrodiphenyl ether have been broadly used as herbicides for initial period paddy field.

However, since these compounds are insufficient in the residual efficacy and inconvenient in that it is difficult to completely control weeds when their use time is missed, it has been desired to develop herbicides for paddy field, having a higher herbicidal activity and a safer selectivity than those of the above-mentioned known diphenyl ether compounds, and also a herbicidal activity capable of controlling perennial weeds of paddy field which are difficult to control.

On the other hand, 2,4-dichloro-4'-nitrodiphenyl ether has been broadly used as a herbicide for dry field crops, and besides, certain diphenyl ether compounds have been known, but since these compounds are insufficient in the efficacy against broad-leaved weeds, it has been also desired to develop herbicides for dry field crops, having a higher herbicidal activity and a safer selectivity than those of these known diphenyl ether compounds.

SUMMARY OF THE INVENTION

An object of the present invention is to provide novel diphenyl ether derivatives having a superior herbicidal activity.

Another object of the present invention is to provide novel herbicides having selectivity and residual efficacy and capable of controlling even perennial weeds which are difficult to control.

In accordance with the present invention, there are provided novel diphenyl ether compounds expressed by the following general formula I and herbicides containing at least one of them as an active ingredient:

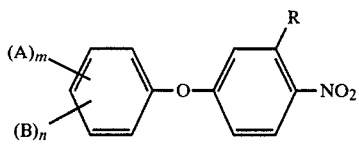

wherein
(1) A and B each represent a halogen atom, a lower alkyl group or a halogen-substituted lower alkyl group;
(2) m and n each represent an integer of 0~3, and m+n=0~3; and
(3) R represents

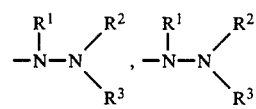

(this group being a group having a cyclic group containing one nitrogen atom therein),

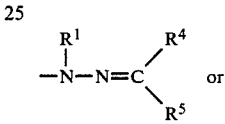 or

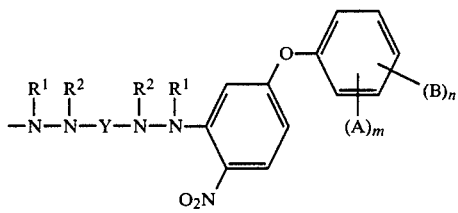

(in the case of this group, the general formula I constitutes two molecules bonded by Y),
wherein
(a) $R^1$ represents hydrogen atom, an alkyl group, preferably a lower alkyl group, a lower alkenyl group, an alkynyl group, an unsubstituted phenyl group, a substituted phenyl group, preferably a halogen-substituted phenyl group, an alkoxycarbonyl group, preferably a lower alkoxycarbonyl group, an unsubstituted phenoxycarbonyl group, a substituted phenoxycarbonyl group, preferably a halogen-substituted phenoxycarbonyl group, an alkylcarbamoyl group, preferably a lower alkylcarbamoyl group, an alkyl (thiocarbamoyl) group, an unsubstituted benzoyl group, a substituted benzoyl group, preferably a halogen-substituted benzoyl group, an unsubstituted acyl group or a halogen-substituted acyl group;
(b) $R^2$ and $R^3$ each represent hydrogen atom, an alkyl group, preferably a lower alkyl group, a lower alkenyl group, a cycloalkyl group, an unsubstituted phenyl group, and O,O-dialkylthiophosphoryl group,

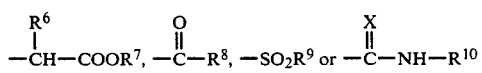

wherein (i) $R^6$ and $R^7$ each represent hydrogen atom or a lower alkyl group;

(ii) $R^8$ represents hydrogen atom, an alkyl group, preferably a lower alkyl group, a lower alkenyl group, unsubstituted phenyl group, a substituted phenyl group, preferably a halogen-substituted phenyl group, benzyl group, a halogen-substituted lower alkyl group, a substituted-phenoxy, substituted lower alkyl group, an unsubstituted phenoxy, substituted lower alkyl group, a lower alkoxy-substituted lower alkyl group, a carboxy-substituted alkyl group, preferably a carboxy-substituted lower alkyl group, a lower alkoxycarbonyl group, an alkoxycarbonyl-substituted alkyl group, preferably an alkoxycarbonyl-substituted lower alkyl group, a carboxy-substituted lower alkenyl group, an alkoxycarbonyl-substituted lower alkenyl group, acetyl group, an alkylthio group, phenoxy group or a lower alkoxy group;

(iii) $R^9$ represents a lower alkyl group, unsubstituted phenyl group, a substituted phenyl group, preferably a lower alkyl-substituted phenyl group or an alkylamino group, preferably a lower alkylamino group;

(iv) X represents oxygen atom or sulfur atom;

(v) $R^{10}$ represents hydrogen atom, an alkyl group, a lower alkenyl group, a cycloalkyl group, unsubstituted phenyl group or a substituted phenyl group, preferably a halogen-substituted phenyl group; and (vi) 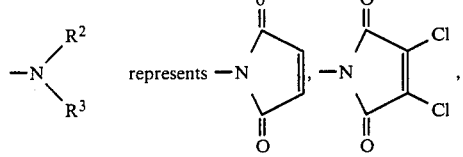 represents

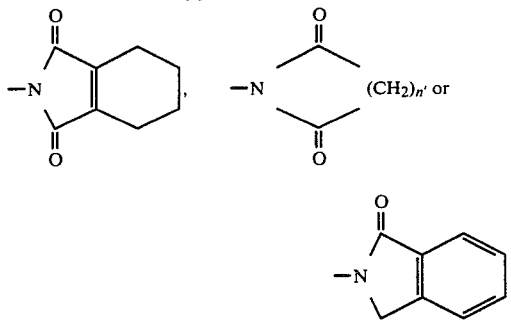

wherein
n' represents an integer of 2–5;

(c) $R^4$ and $R^5$ each represent hydrogen atom, a halogen atom, an alkyl group, a lower alkenyl group, unsubstituted phenyl group, a styryl group, a lower alkoxy group, a halogen-substituted lower alkyl group, a hydroxy-substituted lower alkyl group, a cyano-substituted lower alkyl group, a carboxy-substituted lower alkyl group, a lower alkoxycarbonyl-substituted lower alkyl group, a lower alkylthio group, a furyl group or $R^4$ and $R^5$ together form an alkylene group; and (d) Y represents

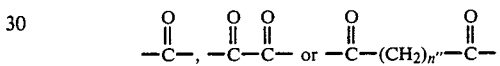

wherein n" represents an integer of 1–4.

DETAILED DESCRIPTION OF THE INVENTION

Examples of the compounds of the present invention represented by the above-mentioned general formula I are illustrated in Table 1 and more specifically in Table 2.

TABLE 1

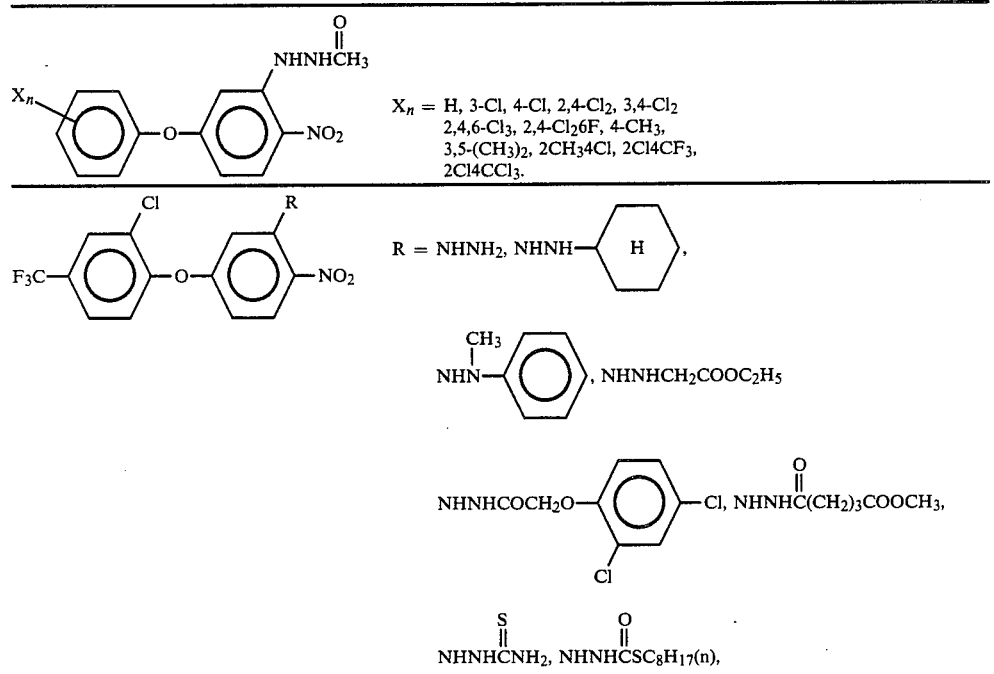

TABLE 1-continued
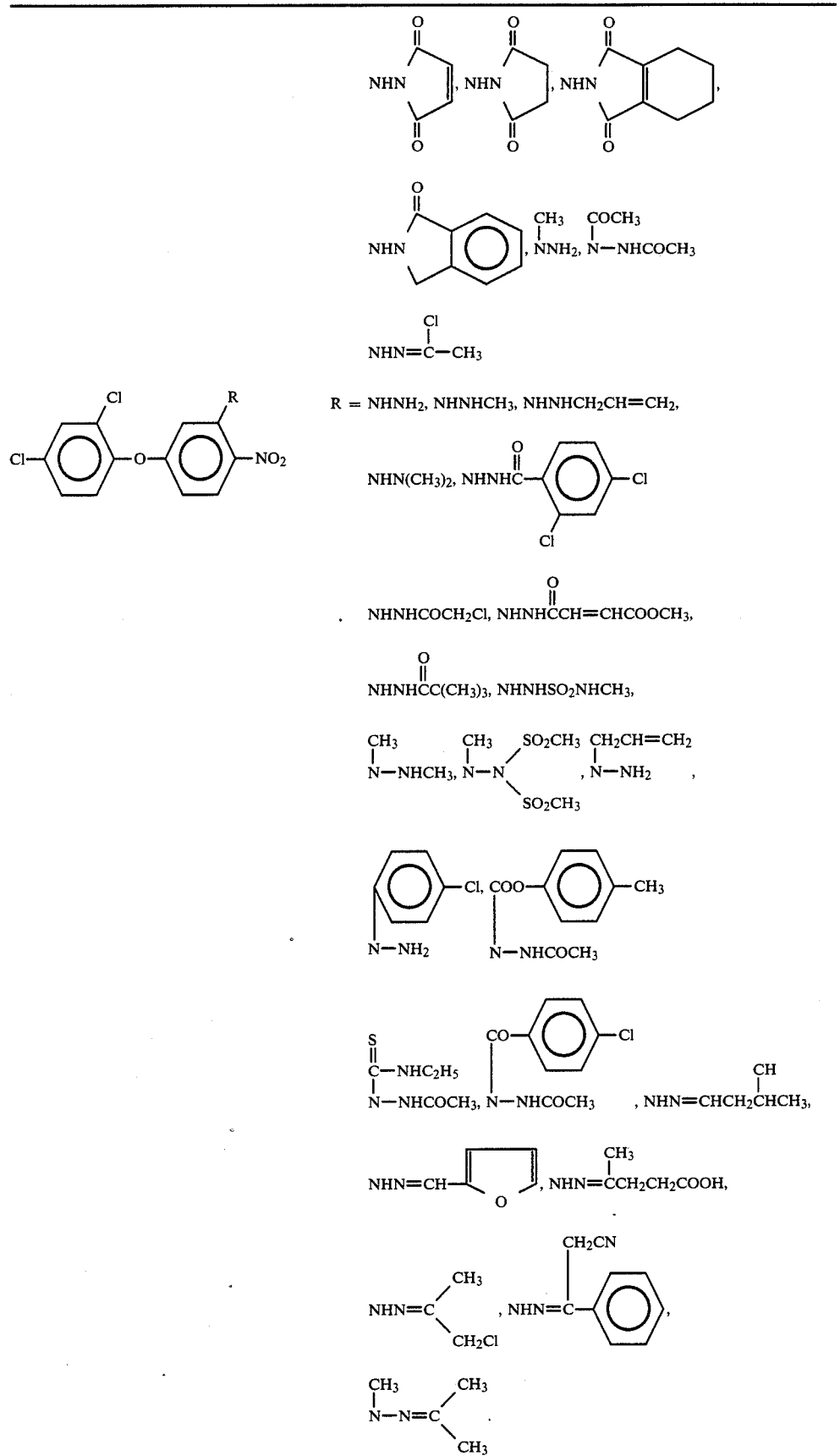

TABLE 1-continued

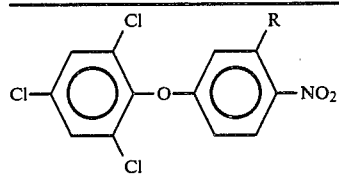
R = NHNHC$_4$H$_9$(n), NHNH$\overset{O}{\overset{\|}{C}}$H,

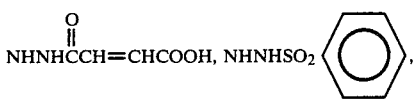

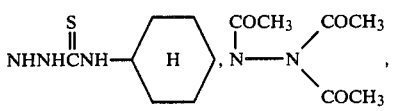

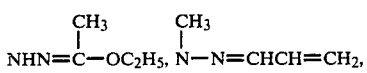

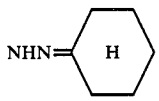

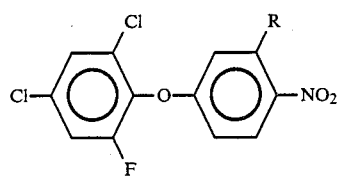
R = NHNH$\overset{O}{\overset{\|}{C}}$C(CH$_3$)$_3$, NHNHSO$_2$CH$_3$, NHNHCOOCH$_3$, $\overset{CH_3}{\overset{|}{N}}$—NHCOCH$_3$, NHN=CHCH$_3$,

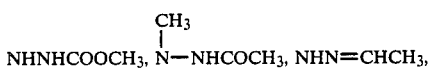

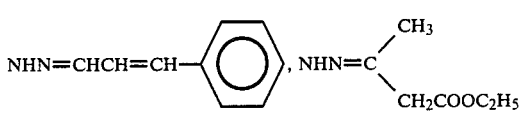

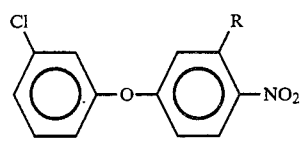

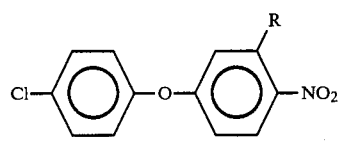

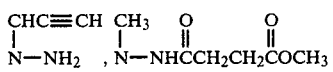

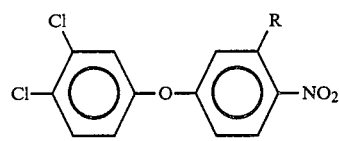
R = NHNH$\overset{O}{\overset{\|}{C}}$C$_2$H$_5$

The novel diphenyl ether compounds of the present invention are superior in controlling weeds of paddy field. They can be used for either the treatment of filled-water prior to occurrence of weeds or the treatment during the growth period in the paddy field where transplantation has been carried out. The compounds of the present invention exhibit a superior herbicidal activity against Smallerflower umbrellaplant, Scirpus juncoides and *Eleocharis kuroguwai*, belonging to Cyperaceae, not to mention Barnyardgrass which is a seriously harmful weed in paddy field, Narrowleaf waterplantain and *Sagittaria trifolia* belonging to Alismataceae, *Monochria vaginalis, Rotala indica, Ludwigia prostrata* and *Eclipta prostrata* which are annular broad-leaf weeds, etc., and have a high selectivity that the phytotoxicity upon transplanted aquatic rice is very small.

Further, the compounds have much superior specific features that they exhibit a superior herbicidal activity and residual efficacy in the soil treatment prior to occurrence of weeds and the treatment of stems and leaves as well as soil, against weeds which raise problems in the dry field crops, such as Crabgrass, Foxtail, Barnyardgrass, Bluegrass, Foxtailgrass, Johnsongrass, Bermudagrass, Quackgrass, Redroot pigweed, Lambsquarters, Smartweed, Velvet leaf, Morningglory, Hertleaf cocklebur, *Rumex japonicus,* Wild mustard, Shepherdspurse, etc., and also have no phytotoxicity upon soybean and peanut belonging to Leguminosae, cotton, corn, wheat, etc., and further, have only a slight phytotoxicity even in the treatment in a higher concentration.

The novel compounds represented by the general formula I may be prepared, for example, according to the following reaction, starting from compounds of formula II which are known and may be prepared, for example, by the processes disclosed in Japanese Patent Kokai No. 49-236, No. 50-37740 and 54-95527.

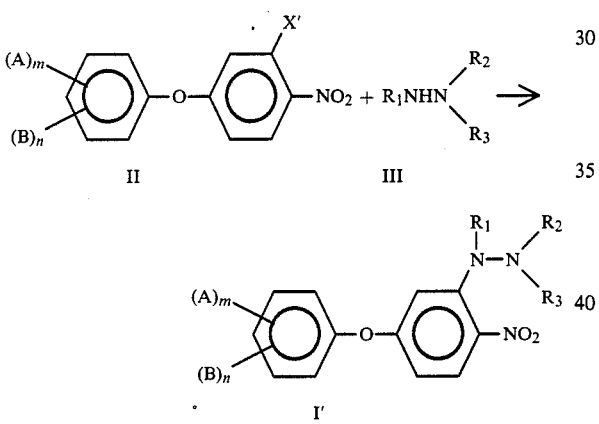

wherein X' stands for a halogen atom, nitro group or a phenoxy group represented by the formula,

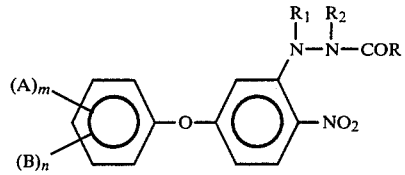

$R_1$, $R_2$ and $R_3$ each stand for hydrogen or a lower alkyl group, and $(A)_m$ and $(B)_n$ are as defined in the general formula I.

When the compound of the general formula II is dissolved in a suitable organic solvent, e.g. benzene, dioxane or dimethylformamide and alkylhydrazine of the general formula III is added, reaction is easily carried out so that the compounds of the general formula I' can be obtained with a high yield.

Using the compounds of the formula I' which are of course included in the present invention, various compounds of the formula I can be prepared by per se known processes as illustrated hereunder:

(1) Formula I' + RCOCl or (RCO)₂O ⟶

$R_{1\sim 2}$ = H or lower alkyl
$R_3$ = H

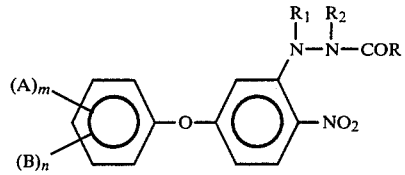

(2) Formula I' + RCOR' ⟶

$R_1$ = H or lower alkyl
$R_{2\sim 3}$ = H

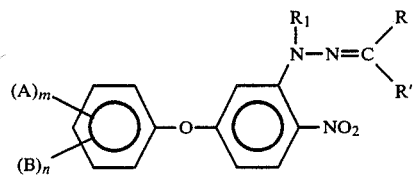

(3) Formula I' + CS₂ + RI $\xrightarrow{\text{Alkali}}$ $R_1$ = H or lower alkyl
$R_{2\sim 3}$ = H

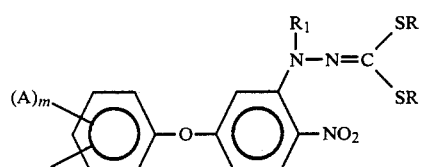

(4) Formula I' + RCHO ⟶

$R_1$ = H or lower alkyl
$R_{2\sim 3}$ = H

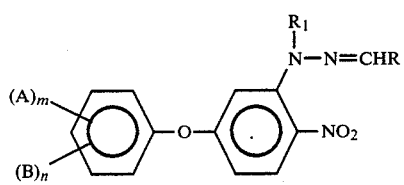

(5) Formula I' + (RO)₃—CR' ⟶

$R_1$ = H or lower alkyl
$R_{2\sim 3}$ = H

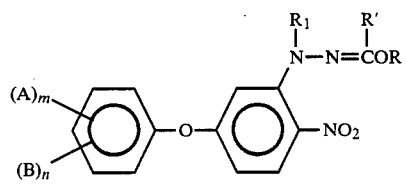

Formula I′ + ClCH₂COOR ⟶ (6)

R₁₋₂ = H or lower alkyl
R₃ = H

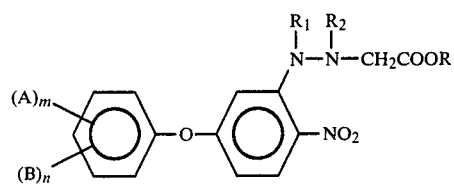

Formula I′ + ClP(=X)(OR)(OR) ⟶ (7)

X = O, S
R₁₋₂ = H or lower alkyl
R₃ = H

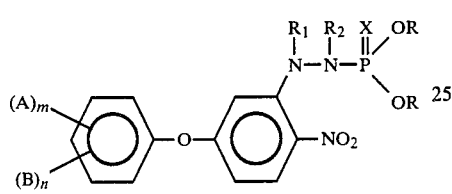

Formula I′ + ClSO₂R ⟶ (8)

R₁₋₂ = H or lower alkyl
R₃ = H

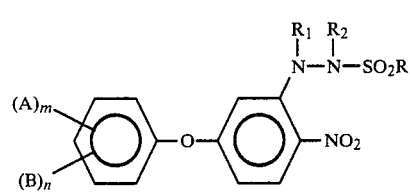

Formula I′ + ClCOR (S) ⟶ (9)

R₁₋₂ = H or lower alk.
R₃ = H

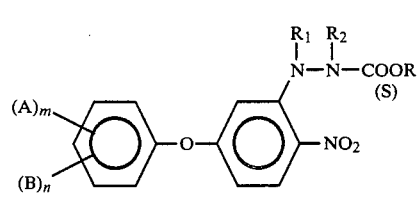

Formula I′ + RNCO ⟶ (10)

R₁₋₂ = H or low. alk.
R₃ = H

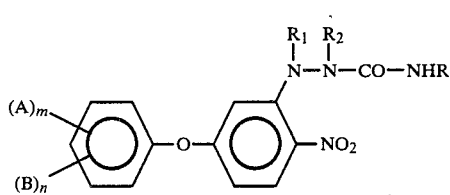

Formula I′ + RNCS ⟶ (11)

R₁₋₂ = H or low. alk.
R₃ = H

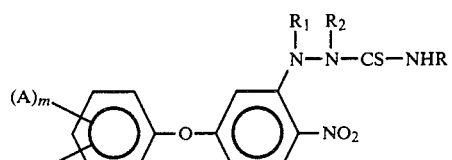

Formula I′ + O=⟨ketone⟩=O, R ⟶ (12)

R₁ = H or low. alk.
R₂ = H (structure with N=N and two acyl groups, R)

Formula I′ + COCl₂ ⟶ (13)

R₁₋₂ = H or low. alk.
R₃ = H

{ (A)ₘ/(B)ₙ–⌬–O–⌬(NO₂)–N(R₁)–N(R₂)–C=O }₂

Formula I′ + ClC(O)(CH₂)ₙC(O)Cl ⟶ (14)

R₁₋₂ = H or low. alk.
R₃ = H

{ (A)ₘ/(B)ₙ–⌬–O–⌬(NO₂)–N(R₁)–N(R₂)–C(O)(CH₂)ₙC(O)– }₂

Herbicidal activity compounds of the formula I may be prepared according to the following reactions, starting from other derivatives than the compounds of the formula I′:

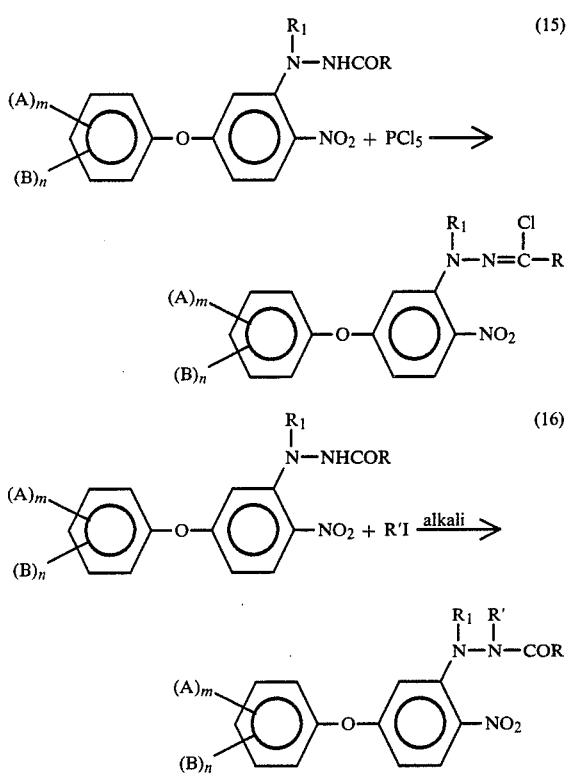

Next, the preparation of the compounds of the general formula I will be illustrated in more detail, by way of the following Examples at the beginning of which the compound number set forth in Table 2 is indicated.

EXAMPLE 1

Preparation of 2-chloro-4-trifluoromethyl-3'-hydrazino-4'-nitrodiphenyl ether (compound No. 19)

2-Chloro-4-trifluoromethyl-3',4'-dinitrodiphenyl ether (7.2 g) and dioxane (50 ml) were introduced into a 100 ml four-neck flask, and after dissolution, hydrazine hydrate (2 g) was dropwise added at 5°-10° C., followed by stirring at 25°-30° C. for 2 hours. After completion of the reaction, the reaction liquid was discharged into 200 ml of water, and the resulting precipitated crystal was collected by filtration, washed with water and dried. The crystal thus obtained was recrystallized from ethanol to obtain 5 g of an objective product having a melting point of 131.5°-132° C.

EXAMPLE 2

Preparation of 2,4-dichloro-3'-hydrazino-4'-nitrodiphenyl ether (compound No. 7)

2,4-Bis(2,4-dichlorophenoxy)nitrobenzene (44.5 g) and dioxane (100 ml) were introduced into a 200 ml four-neck flask, and after dissolution, hydrazine hydrate (15 ml) was added, followed by stirring at 60°-80° C. for 8 hours. The resulting liquid after completion of the reaction was discharged into water, and the resulting precipitated crystal was collected by filtration, washed with water and dried. The crystal thus obtained was recrystallized from ethanol to obtain 26 g of an objective product having a melting point of 124°-125° C.

EXAMPLE 3

Preparation of 3,5-dimethyl-3'-(2-acetylhydrazino)-4'-nitrodiphenyl ether (compound No. 18)

3,5-Dimethylphenol (7 g), potassium carbonate (7.5 g) and dimethylformamide (100 ml) were introduced into a 200 ml four-neck flask, and 2-acetyl-1-(5-chloro-2-nitrophenyl) hydrazine (11 g) was added, followed by stirring at 140°-145° C. for 5 hours. The resulting liquid after completion of the reaction was discharged into water and extracted with a solvent mixture of benzene/ethyl acetate, followed by washing with water and drying on anhydrous sodium sulfate. After drying, the solvents were distilled off under reduced pressure, followed by purification, by means of a silica gel column employing benzene/ethyl acetate (1:1) as a developing solvent, to obtain 2 g of an objective product having a melting point of 192°-193° C.

EXAMPLE 4

Preparation of 2,4-dichloro-3'-(ethoxymethylene)-hydrazino-4'-nitrodiphenyl ether (compound No. 10)

2,4-Dichloro-3'-hydrazino-4'-nitrodiphenyl ether (2 g) and benzene (50 ml) were introduced into a 100 ml four-neck flask, and after dissolution, ethyl orthoformate (1 ml) and conc. sulfuric acid (one drop) were added, followed by stirring under reflux for 30 minutes. The resulting reaction liquid was cooled, washed with water and dried on anhydrous sodium sulfate, followed by distilling off benzene under reduced pressure and recrystallization from ethanol, to obtain 2.1 g of an objective product having a melting point of 135°-136° C.

EXAMPLE 5

Preparation of 2-chloro-4-trifluoromethyl-3'-(2-n-butylhydrazino)-4'-nitrodiphenyl ether (compound No. 21) and 2-chloro-4-trifluoromethyl-3'-(1-n-butylhydrazino)-4'-nitrodiphenyl ether (compound No. 98)

2-Chloro-4-trifluoromethyl-3',4'-dinitrodiphenyl ether (3.6 g) and dioxane (30 ml) were introuced into a 50 ml four-neck flask, and after dissolution, n-butylhydrazine (2 g) was dropwise added, followed by stirring at room temperature for 4 hours. To the resulting reaction liquid was added about 200 ml of benzene, followed by washing with water, and drying on anhydrous sodium sulfate. After distilling off benzene under reduced pressure, purification and separation were carried out by means of a silica gel column employing benzene as a developing solvent to obtain liquids of 2-chloro-4-trifluoromethyl-3'-(2-n-butylhydrazino)-4'-nitrodiphenyl ether (1.2 g) and 2-chloro-4-trifluoromethyl-3'-(1-n-butylhydrazino)-4'-nitrodiphenyl ether (1.3 g).

EXAMPLE 6

Preparation of 2-chloro-4-trifluoromethyl-3'-(2,2-dimethylhydrazino)-4'-nitrodiphenyl ether (compound No. 23)

2-Chloro-4-trifluoromethyl-3',4'-dinitrodiphenyl ether (7.2 g) and dioxane (100 ml) were introduced into a 200 ml four-neck flask, and after dissolution, 1,1-dimethylhydrazine (2.7 g) was added at room temperature, followed by stirring at 50°-60° C. for 5 hours. The resulting reaction liquid was cooled and then discharged into water, followed by extraction with benzene and drying on anhydrous sodium sulfate. After distilling off benzene under reduced pressure, purification was carried out by means of a silica gel column employing benzene as a developing solvent to obtain 7.7 g of a liquid as an objective product.

EXAMPLE 7

Preparation of 2-chloro-4-trifluoromethyl-3'-(2-ethoxycarbonylmethylhydrazino)-4'-nitrodiphenyl ether (compound No. 25)

2-Chloro-4-trifluoromethyl-3'-hydrazino-4'-nitrodiphenyl ether (3.5 g), triethylamine (1 g) and toluene (100 ml) were introduced into a 200 ml four-neck flask, and after dissolution, ethyl bromoacetate (1.7 g) was added, followed by stirring under reflux for 10 hours. After the stirring, the resulting reaction material was discharged into water, and the resulting toluene layer was washed with dilute hydrochloric acid and water and dried on anhydrous sodium sulfate. Toluene was distilled off under reduced pressure and the resulting oily substance was purified by means of a silica gel column employing benzene as a developing solvent to obtain 1 g of an objective product having a melting point of 99°–100° C.

EXAMPLE 8

Preparation of 2-chloro-4-trifluoromethyl-3'-(o,o-diethylthiophosphonylhydrazino)-4'-nitrodiphenyl ether (compound No. 26)

2-Chloro-4-trifluoromethyl-3'-hydrazino-4'-nitrodiphenyl ether (3.4 g) triethylamine (1.1 g) and isopropanol (100 ml) were introduced into a 200 ml four-neck flask, and after dissolution, O,O-diethylthiophosphonyl chloride (1.9 g) was dropwise added at room temperature, followed by stirring at 50°–60° C. for 4 hours. The resulting material was cooled and then discharged into water. The resulting oily substance was extracted twice with 150 ml of benzene, followed by washing with dilute hydrochloric acid, sodium bicarbonate aqueous solution and water and drying on anhydrous sodium sulfate. The solvent was distilled off under reduced pressure, to give 5 g of an oily substance, which was purified by means of a silica gel column employing benzene as a developing solvent to obtain 4 g of an objective product having a melting point of 70°–71° C.

EXAMPLE 9

Preparation of 2-chloro-4-trifluoromethyl-3'-(2-formylhydrazino)-4'-nitrodiphenyl ether (compound No. 27)

2-Chloro-4-trifluoromethyl-3'-hydrazino-4'-nitrophenyl ether (3.4 g), formic acid (0.5 g) and ethanol (30 ml) were introduced into a 50 ml four-neck flask, followed by dissolution and then stirring under reflux for 2 hours. After cooling, ethanol was distilled off under reduced pressure. A solid substance thus obtained was recrystallized from benzene/ethanol to obtain 1.6 g of an objective product having a melting point of 176°–177° C.

EXAMPLE 10

Preparation of 2-chloro-4-trifluoromethyl-3'-(2-crotonoylhydrazino)-4'-nitrodiphenyl ether (compound No. 33)

2-Chloro-4-trifluoromethyl-3'-hydrazino-4'-nitrodiphenyl ether (3.5 g) and glacial acetic acid (50 ml) were introduced into a 100 ml four-neck flask, and after dissolution, crotonic anhydride (2 g) was added at room temperature, followed by stirring at 80°–90° C. for 3 hours. The resulting reaction liquid was discharged into 300 ml of water and extracted with ethyl acetate, followed by washing with water and then drying on anhydrous sodium sulfate. The solvent was distilled off under reduced pressure, and the resulting material was recrystallized from benzene/n-hexane to obtain 2.8 g of an objective product having a melting point of 170°–171° C.

EXAMPLE 11

Preparation of 2-chloro-4-trifluoromethyl-3'-(2-chloroacetylhydrazino)-4'-nitrodiphenyl ether (compound No. 37)

2-Chloro-4-trifluoromethyl-3'-hydrazino-4'-nitrodiphenyl ether (3.5 g), triethylamine (1.2 g) and benzene (100 ml) were introduced into a 200 ml four-neck flask, and after dissolution, chloroacetyl chloride (1.3 g) was dropwise added, followed by heating under reflux with stirring for 2 hours. The resulting material was cooled and then discharged into water, followed by collecting the resulting crystal by filtration, washing with water and drying. The resulting raw crystal was recrystallized from benzene to obtain 2.9 g of an objective product having a melting point of 188°–188.5° C.

EXAMPLE 12

Preparation of 2-chloro-4-trifluoromethyl-3'-(3-ethoxycarbonylpropionyl)hydrazino-4'-nitrodiphenyl ether (compound No. 44)

2-Chloro-4-trifluoromethyl-3'-hydrazino-4'-nitrodiphenyl ether (2 g), pyridine (0.6 ml) and tetrahydrofuran (20 ml) were introduced into a 50 ml four-neck flask, and after dissolution, acid chloride of monoethyl succinate (1 g) was slowly added under cooling at −5°–0° C., followed by stirring at room temperature for one hour. The resulting reaction liquid was discharged into water and extracted with benzene, followed by drying on anhydrous sodium sulfate. Benzene was distilled off under reduced pressure and the resulting material was purified by means of a silica gel column employing benzene/ethyl acetate (4:1) as a developing solvent to obtain 1 g of an objective product having a melting point of 117°–118° C.

EXAMPLE 13

Preparation of 2-chloro-4-trifluoromethyl-3'-(2-p-tosylhydrazino)-4'-nitrodiphenyl ether (compound No. 49)

2-Chloro-4-trifluoromethyl-3'-hydrazino-4'-nitrodiphenyl ether (3.4 g) and pyridine (30 ml) were introduced into a 100 ml four-neck flask, and p-toluenesulfonyl chloride (2 g) was added at room temperature, followed by stirring for one hour and allowing the resulting material to stand overnight. The resulting reaction liquid was discharged into water and extracted with benzene, followed by washing with water and drying on anhydrous sodium sulfate. After distilling off the solvent under reduced pressure, the resulting material was purified by means of a silica gel column employing benzene/ethyl acetate (4:1) as a developing solvent to obtain 4 g of an objective product having a melting point of 146°–147° C.

EXAMPLE 14

Preparation of
2-chloro-4-trifluoromethyl-3'-ethoxycarbonylhydrazino-4'-nitrodiphenyl ether (compound No. 53)

2-Chloro-4-trifluoromethyl-3'-hydrazino-4'-nitrodiphenyl ether (3.5 g), pyridine (0.9 g) and toluene (50 ml) were introduced into a 100 ml four-neck flask, and after dissolution and subsequent cooling to 0°–5° C., ethyl chlorocarbonate (1.2 g) was slowly added, followed by stirring at the same temperature for one hour. Toluene was distilled off under reduced pressure from the resulting reaction liquid, and 100 ml of water was added, followed by collecting the resulting crystal by filtration. A raw crystal thus obtained was recrystallized from ethanol/water to obtain 2.9 g of an objective product having a melting point of 118°–119° C.

EXAMPLE 15

Preparation of
2-chloro-4-trifluoromethyl-3'-(n-octylthio)carbonylhydrazino-4'-nitrodiphenyl ether (compound No. 58)

2-Chloro-4-trifluoromethyl-3'-hydrazino-4'-nitrodiphenyl ether (3.5 g), triethylamine (1 g) and benzene (100 ml) were introduced into a 200 ml four-neck flask, and after dissolution, n-octylthiocarbonyl chloride (2.1 g) was dropwise added at room temperature, followed by stirring at 55°–60° C. for 3 hours. The resulting material was cooled and then discharged into water, followed by separating the resulting benzene layer, washing with water and drying on anhydrous sodium sulfate. Benzene was then distilled off, and the resulting material was purified by means of a silica gel column employing benzene as a developing solvent to obtain 2.3 g of an objective product having a melting point of 83°–84° C.

EXAMPLE 16

Preparation of
2-chloro-4-trifluoromethyl-3'-(4-ethylsemicarbazido)-4'-nitrodiphenyl ether (compound No. 60)

2-Chloro-4-trifluoromethyl-3'-hydrazino-4'-nitrodiphenyl ether (3.4 g) and toluene (50 ml) were introduced into a 100 ml four-neck flask. After dissolution, ethyl isocyanate (1.4 g) dissolved in 20 ml of toluene and 2-3 drops of dibutyltin laurate were dropwise added at room temperature, and temperature was slowly elevated, followed by stirring under reflux for one hour. After cooling, the resulting precipitated crystal was collected by filtration and washed with toluene to obtain 3.3 g of an objective product having a melting point of 184°–185° C.

EXAMPLE 17

Preparation of
2-chloro-4-trifluoromethyl-3'-thiosemicarbazido-4'-nitrodiphenyl ether (compound No. 65)

2-Chloro-3-trifluoromethyl-3'-hydrazino-4'-nitrodiphenyl ether (3.5 g), ethanol (50 ml), conc. hydrochloric acid (0.9 ml) and sodium thiocyanate (0.8 g) were introduced into a 100 ml four-neck flask, and agitated under reflux for 6 hours. Ethanol was then distilled off under reduced pressure, followed by adding 200 c.c. of water, collecting the resulting crystal by filtration and recrystallization from ethanol/water to obtain 0.9 g of an objective product having a melting point of 180.5°–183° C.

EXAMPLE 18

Preparation of
2-chloro-4-trifluoromethyl-3'-(4-ethyl)thiosemicarbazido-4'-nitrodiphenyl ether (compound No. 67)

2-Chloro-4-trifluoromethyl-3'-hydrazino-4'-nitrodiphenyl ether (3.4 g) and toluene (100 ml) were introduced into a 200 ml four-neck flask, and after dissolution, ethyl isothiocyanate (0.9 g) and dibutyltin laurate (2-3 drops) were dropwise added, followed by stirring under reflux for 10 hours. After cooling, toluene was distilled off under reduced pressure to obtain 5 g of an oily substance containing a crystal, to which a small amount of benzene was added. The resulting crystal was collected by filtration to obtain 1.7 g of an objective product having a melting point of 180°–181° C.

EXAMPLE 19

Preparation of
2-chloro-4-trifluoromethyl-3'-(dichloromaleninimidoyl)amino-4'-nitrodiphenyl ether (compound No. 71)

2-Chloro-4-trifluoromethyl-3'-hydrazino-4'-nitrodiphenyl ether (3.4 g), dichloromaleic anhydride (1.7 g) and acetic acid (100 ml) were introduced into a 200 ml four-neck flask, followed by stirring at 110° C. for 2 hours. After cooling, the resulting material was discharged into water, and precipitated crystal was collected by filtration, followed by washing with water and a small amount of ethanol to obtain 3.3 g of an objective product having a melting point of 149°–150° C.

EXAMPLE 20

Preparation of
N-{5-(2-chloro-4-trifluoromethylphenoxy)-2-nitrophenyl}amino-2,3-dihydroisoindolinone (compound No. 73)

2-Chloro-4-trifluoromethyl-3'-hydrazino-4'-nitrodiphenyl ether (3.5 g), triethylamine (2.2 g) and dioxane (100 ml) were introduced into a 200 ml four-neck flask, and after dissolution, 2-chloromethylbenzoyl chloride (1.9 g) was added little by little at room temperature, followed by stirring at 95°–100° C. for 3 hours. After cooling, the resulting material was discharged into water and extracted with benzene, followed by washing with an aqueous solution of sodium hydrogen sulfate and water and drying with anhydrous sodium sulfate. After drying, benzene was distilled off under reduced pressure, and the resulting material was purified by means of a silica gel column employing benzene/ethyl acetate (95:5) as a developing solvent to obtain 0.9 g of an objective product having a melting point of 207°–208° C.

EXAMPLE 21

Preparation of 2-chloro-4-trifluoromethyl-3'-(1-methylhydrazino)-4'-nitrodiphenyl ether (compound No. 76)

2-Chloro-4-trifluoromethyl-3',4'-dinitrodiphenyl ether (36 g) and dioxane (300 ml) were introduced into a 500 ml four-neck flask, and methylhydrazine (9 g) was dropwise added at 20° C. or lower, followed by stirring at room temperature for 2 hours. The resulting reaction liquid was discharged into water and extracted with benzene, followed by washing with water and drying on anhydrous sodium sulfate. Benzene was distilled off under reduced pressure and recrystallization from ethanol was carried out to obtain 24 g of an objective product having a melting point of 96°–97° C.

EXAMPLE 22

Preparation of 2-chloro-4-trifluoromethyl-3'-(1-methyl-2-methylsulfonylhydrazino)-4'-nitrodiphenyl ether (compound No. 85) and 2-chloro-4-trifluoromethyl-3'-{1-methyl-2,2-bis(methylsulfonyl)hydrazino}-4'-nitrodiphenyl ether (compound No. 86)

2-Chloro-4-trifluoromethyl-3'-(1-methylhydrazino)-4'-nitrodiphenyl ether (3.6 g), triethylamine (1 g) and benzene (100 ml) were introduced into a 200 ml four-neck flask, and methanesulfonyl chloride (1.7 g) was dropwise added while temperature was maintained at 15° C. or lower, followed by stirring at room temperature for one hour. The resulting reaction liquid was discharged into water, and the resulting benzene layer was washed with water and dried on anhydrous sodium sulfate. After drying, benzene was distilled off under reduced pressure, and the resulting liquid was purified by means of a silica gel column employing benzene/ethyl acetate (10:1) as a developing solvent to obtain 0.8 g of 2-chloro-4-trifluoromethyl-3'-(1-methyl-2-methylsulfonylhydrazino)-4'-nitrodiphenyl ether having a melting point of 117°–118° C. and 2.5 g of 2-chloro-4-trifluoromethyl-3'-{1-methyl-2,2-bis(methylsulfonyl)hydrazino}-4'-nitrodiphenyl ether having a melting point of 160°–161.5° C.

EXAMPLE 23

Preparation of 2-chloro-4-trifluoromethyl-3'-{1-methyl-2-(N-methylsulfamoyl)hydrazino}-4'-nitrodiphenyl ether (compound No. 87)

2-Chloro-4-trifluoromethyl-3'-(1-methylhydrazino)-4'-nitrodiphenyl ether (3.6 g), triethylamine (1 g) and benzene (100 ml) were introduced into a 200 ml four-neck flask, and methylaminosulfamoyl chloride (1.9 g) was dropwise added at 15° C. or lower, followed by stirring at room temperature for one hour. The resulting material was discharged into water, and the resulting benzene layer was twice washed with water and then dried on anhydrous sodium sulfate. Benzene was distilled off under reduced pressure, followed by recrystallization from benzene/n-hexane (1:1) to obtain 3 g of an objective product having a melting point of 124°–126° C.

EXAMPLE 24

Preparation of 2-chloro-4-trifluoromethyl-3'-(1,2,2-triacetylhydrazino)-4'-nitrodiphenyl ether (compound No. 102)

2-Chloro-4-trifluoromethyl-3'-hydrazino-4'-nitrodiphenyl ether (3.5 g), triethylamine (1.2 g) and benzene (100 ml) were introduced into a 200 ml four-neck flask, and after dissolution, acetyl chloride (2.6 g) was dropwise added at 5°–10° C., followed by stirring at 40° C. for 2 hours. After cooling, the resulting material was discharged into water, and the resulting crystal was collected by filtration, followed by purification by means of a silica gel column employing benzene/ethyl acetate (4:1) as a developing solvent to obtain 4 g of an objective product having a melting point of 106°–107° C.

EXAMPLE 25

Preparation of 2-chloro-4-trifluoromethyl-3'-(2-acetyl-1-ethoxycarbonylhydrazino)-4'-nitrodiphenyl ether (compound No. 103)

2-Chloro-4-trifluoromethyl-3'-(2-acetylhydrazino)-4-nitrodiphenyl ether (3.9 g), triethylamine (1.2 g) and benzene (100 ml) were introduced into a 200 ml four-neck flask, and after dissolution, ethyl chlorocarbonate (1.2 g) was dropwise added at 5°–10° C., followed by stirring at 40° C. for 2 hours. The resulting reaction liquid was discharged into water, and the resulting crystal was collected by filtration, followed by purification by means of a silica gel column employing benzene/ethyl acetate (4:1) as a developing solvent to obtain 1.5 g of an objective product having a melting point of 134°–135° C.

EXAMPLE 26

Preparation of 2-chloro-4-trifluoromethyl-3'-(2-acetyl-1-ethylcarbamoylhydrazino)-4'-nitrodiphenyl ether (compound No. 104)

2-Chloro-4-trifluoromethyl-3'-(2-acetylhydrazino)-4'-nitrodiphenyl ether (3.9 g) and toluene (100 ml) were introduced into a 200 ml four-neck flask, and then a solution obtained by dissolving 0.8 g of ethyl isocyanate in 5 ml of toluene and one drop of dibutyltin laurate were added at room temperature, followed by stirring under reflux for 6 hours. Toluene was then distilled off under reduced pressure, followed by purification by means of a silica gel column employing benzene/ethyl acetate (4:1) as a developing solvent to obtain 3.5 g of an oily substance as an objective product.

EXAMPLE 27

Preparation of 2-chloro-4-trifluoromethyl-3'-(n-heptylidenehydrazino)-4'-nitrodiphenyl ether (compound No. 113)

2-Chloro-4-trifluoromethyl-3'-hydrazino-4'-nitrodiphenyl ether (3.5 g) and dioxane (30 ml) were introduced into a 50 ml four-neck flask, and after dissolution, n-heptylaldehyde (1.5 g) and 3 drops of conc. hydrochloric acid were added at room temperature, followed by stirring 4 hours. The resulting material was discharged into 200 ml of water, followed by collecting the resulting crystal by filtration and recrystallization from ethanol to obtain 3.6 g of an objective product having a melting point of 93°–94° C.

EXAMPLE 28

Preparation of 2-chloro-4-trifluoromethyl-3'-(1-chloroethylidene)hydrazino-4'-nitrodiphenyl ether (compound No. 123)

2-Chloro-4-trifluoromethyl-3'-(2-acetylhydrazino)-4'-nitrodiphenyl ether (4.5 g) and phosphorus pentachloride (2.9 g) were introduced into a 50 ml four-neck flask, followed by stirring at 70° C. for about one hour until no hydrogen chloride gas was evolved. After cooling, benzene was added, followed by extraction. The resulting benzene solution was decanted and used for the following reaction:

Phenol (3.2 g) and benzene (100 ml) were introduced into a 200 ml four-neck flask, and the benzene solution prepared above was dropwise added while temperature was maintained at 10°–15° C., followed by stirring at 20° C. for 3 hours. Hydrogen chloride gas was removed employing nitrogen gas, followed by distilling off benzene under reduced pressure to obtain 10 g of an oily substance, which was then purified by means of a silica gel column employing benzene as a developing solvent to obtain 2.6 g of an objective product having a melting point of 108°–113° C.

EXAMPLE 29

Preparation of 2-chloro-4-trifluoromethyl-3'-(2-isopropylidenehydrazino)-4'-nitrodiphenyl ether (compound No. 124)

2-Chloro-4-trifluoromethyl-3'-hydrazino-4'-nitrodiphenyl ether (3.5 g) and acetone (50 ml) were introduced into a 100 ml four-neck flask, and after dissolution, the resulting solution was allowed to stand at room temperature for one hour. Acetone was distilled off under reduced pressure from the reaction liquid to obtain 3.5 g of a raw crystal, which was recrystallized from ethanol to obtain 2.5 g of an objective product having a melting point of 134°–135° C.

EXAMPLE 30

Preparation of 2-chloro-4-trifluoromethyl-3'-{bis(methylthio)methylene}hydrazino-4'-nitrodiphenyl ether (compound No. 140)

2-Chloro-4-trifluoromethyl-3'-hydrazino-4'-nitrodiphenyl ether (3.5 g) and ethanol (60 ml) were introduced into a 200 ml four-neck flask, and carbon disulfide (2.3 g) was dropwise added with stirring. A solution obtained by dissolving 1.2 g of potassium hydroxide in ethanol was then added, followed by stirring at room temperature for 30 minutes. Methyl iodide (5 g) was further added, followed by stirring at 45°–50° C. for one hour. The resulting reaction liquid was discharged into water, followed by extraction with benzene and drying with anhydrous sodium sulfate. Solvent was distilled off under reduced pressure, followed by purification by means of a silica gel column employing benzene/n-hexane (1:1) as a developing solvent to obtain 0.5 g of an objective product having a melting point of 121°–124° C.

EXAMPLE 31

Preparation of oxalic acid bis[5-(2-chloro-4-trifluoromethylphenoxy)-2-nitrophenyl]hydrazide (compound No. 171)

2-Chloro-4-trifluoromethyl-3'-hydrazino-4'-nitrodiphenyl ether (7.0 g), triethylamine (2.5 ml) and dioxane (80 ml) were introduced into a 200 ml four-neck flask, and oxalic chloride (1.3 g) was dropwise added with stirring, followed by reaction at room temperature for 2 hours. The resulting reaction liquid was discharged into water, and precipitated crystal was collected by filtration and air-dried. This crystal was recrystallized from a solvent mixture of dioxane/benzene to obtain 6.2 g of an objective product having a melting point of 266°–268° C. (decomposition).

EXAMPLE 32

Preparation of 2-chloro-4-trifluoromethyl-3'-(2-methyl-2-acetylhydrazino)-4'-nitrodiphenyl ether (compound No. 173)

2-Chloro-4-trifluoromethyl-3'-(2-acetylhydrazino)-4'-nitrodiphenyl ether (7.8 g), anhydrous potassium carbonate (2.8 g) and ethanol (100 ml) were introduced into a 200 ml four-neck flask and heated. While the resulting liquid was agitated under reflux, methyl iodide (2.9 g) was added and reaction was carried out for 4 hours. The resulting reaction liquid was discharged into water, and precipitated crystal was collected by filtration, and then recrystallized from methanol to obtain 4.9 g of an objective product having a melting point of 101.5°–102.5° C.

Other compounds included in the above-mentioned general formula I can be also synthesized according to any one of the above-mentioned methods, and the details of the synthesis method therefor will be shown in the item "Synthesis method example No." of the following Table 2.

Next, representative compounds among those of the present invention expressed by the general formula I and their physical properties are illustrated in the following Table 2.

TABLE 2

| Compound No. | Substituents in general formula I $(A)_n$ / $(B)_m$ | R | Synthesis method example No. | Melting point (°C.) (Infrared ray absorption spectra, $cm^{-1}$) | Elemental analysis value % (upper row, observed value; lower row, calculated value) | | | | |
|---|---|---|---|---|---|---|---|---|---|
| | | | | | C | H | N | Cl | F | S |
| 1 | Cl / ⟨O⟩ | —NHNH$_2$ | 1 | 95–97 | 51.66 / 51.53 | 3.78 / 3.60 | 14.88 / 15.02 | 12.24 / 12.68 | — | — |
| 2 | " | —NHNHCCH$_3$ (C=O) | 10 | 151.5–153 | 52.26 / 52.26 | 3.85 / 3.76 | 12.99 / 13.06 | 10.96 / 11.02 | — | — |

TABLE 2-continued

| Compound No. | Substituents in general formula I (A)$_n$ / (B)$_m$ | R | Synthesis method example No. | Melting point (°C.) (Infrared ray absorption spectra, cm$^{-1}$) | Elemental analysis value % (upper row, observed value; lower row, calculated value) | | | | | |
|---|---|---|---|---|---|---|---|---|---|---|
| | | | | | C | H | N | Cl | F | S |
| 3 | " | —NHN=C(CH$_3$)(CH$_3$) | 29 | 105–106 | 56.38 56.34 | 4.56 4.41 | 13.08 13.14 | 11.11 11.09 | — | — |
| 4 | " | —NHN=C(CH$_3$)(C$_9$H$_{19}$(n)) | 29 | (3325, 2920, 1615, 1583, 1465, 1340, 1210, 1145) | 64.01 63.95 | 7.13 7.00 | 9.68 9.73 | 8.53 8.21 | — | — |
| 5 | " | —NHN=C(CH$_3$)(CH$_2$CH$_2$COOH) | 27 | 153–155 | 54.21 54.04 | 4.36 4.27 | 11.02 11.12 | 9.57 9.39 | — | — |
| 6 | " | —NHN=C(SCH$_3$)(SCH$_3$) | 30 | 111–112 | 46.89 46.93 | 3.77 3.68 | 10.85 10.95 | 9.33 9.24 | — | 16.58 16.71 |
| 7 | 2,4-Cl$_2$-phenyl | —NHNH$_2$ | 2 | 124–125 | 45.91 45.88 | 3.02 2.89 | 13.52 13.38 | 22.94 22.57 | — | — |
| 8 | " | —NHNHCOCH$_3$ | 10 | 162–163 | 47.55 47.21 | 3.83 3.11 | 12.01 11.80 | 19.52 19.91 | — | — |
| 9 | " | —NHNHCOC$_2$H$_5$ | 10 | 166–168 | 48.09 48.67 | 3.26 3.54 | 11.19 11.35 | 19.34 19.16 | — | — |
| 10 | " | —NHN=CHOC$_2$H$_5$ | 4 | 135–136 | 49.00 48.67 | 3.66 3.54 | 11.93 11.35 | 18.99 19.16 | — | — |
| 11 | 2,4,6-Cl$_3$-phenyl | —NHNH$_2$ | 1 | 170–171 | 40.98 41.37 | 2.38 2.31 | 12.51 12.05 | 30.53 30.05 | — | — |
| 12 | " | —NHNHCOCH$_3$ | 10 | 218–219 | 43.29 43.05 | 2.97 2.58 | 10.77 10.76 | 27.81 27.23 | — | — |
| 13 | " | —NHN=C(CH$_3$)(CH$_3$) | 29 | 169–170 | 46.20 46.35 | 3.09 3.11 | 11.05 10.81 | 27.48 27.37 | — | — |
| 14 | " | —NHN=C(C$_2$H$_5$)(OC$_2$H$_5$) | 4 | 119–126 | 47.34 47.19 | 3.60 3.73 | 9.18 9.71 | 24.90 24.58 | — | — |
| 15 | 2,4-Cl$_2$-5-F-phenyl | —NHNH$_2$ | 1 | 148.5–149.5 | 43.37 43.39 | 2.87 2.43 | 12.47 12.65 | 21.69 21.35 | 5.57 5.72 | — |
| 16 | " | —NHN=CHCH$_3$ | 27 | 178–179 | 46.36 46.95 | 3.26 2.81 | 11.47 11.73 | 20.34 19.80 | 5.19 5.31 | — |

TABLE 2-continued

| Compound No. | Substituents in general formula I (A)$_n$ / (B)$_m$ | R | Synthesis method example No. | Melting point (°C.) (Infrared ray absorption spectra, cm$^{-1}$) | Elemental analysis value % (upper row, observed value; lower row, calculated value) | | | | | |
|---|---|---|---|---|---|---|---|---|---|---|
| | | | | | C | H | N | Cl | F | S |
| 17 | " | —NHN=C(CH$_3$)(CH$_3$) | 29 | 146–148 | 48.21 / 48.40 | 3.44 / 3.25 | 11.28 / 11.29 | 19.11 / 19.05 | 5.02 / 5.11 | — |
| 18 | 3,5-(CH$_3$)$_2$C$_6$H$_3$ | —NHNHCOCH$_3$ | 3 | 192–193 | 60.87 / 60.85 | 5.63 / 5.43 | 12.97 / 13.30 | — | — | — |
| 19 | 3-Cl-4-CF$_3$C$_6$H$_3$ | —NHNH$_2$ | 1 | 131.5–132 | 44.56 / 44.91 | 3.04 / 2.61 | 11.56 / 12.08 | 10.39 / 10.20 | 16.11 / 16.39 | — |
| 20 | C$_6$H$_5$ | —NHNHCOCH$_3$ | 3 | 133–135 | 59.33 / 58.53 | 4.14 / 4.56 | 14.98 / 14.63 | — | — | — |
| 21 | 3-Cl-4-CF$_3$C$_6$H$_3$ | —NHNHC$_4$H$_9$(n) | 5 | (3400, 2980, 1645, 1515, 1340, 1275, 1150, 1095) | 50.92 / 50.56 | 3.96 / 4.24 | 10.25 / 10.41 | 8.69 / 8.78 | 13.97 / 14.12 | — |
| 22 | " | —NHNH—C$_6$H$_{11}$ | 5 | (2260, 2940, 1630, 1500, 1330, 1265, 1130, 1085) | 52.93 / 53.08 | 4.25 / 4.46 | 10.08 / 9.78 | 8.45 / 9.25 | 13.55 / 13.26 | — |
| 23 | " | —NHN(CH$_3$)(CH$_3$) | 6 | (3320, 2960, 1510, 1335, 1275, 1185, 1140, 1093) | 47.56 / 47.94 | 3.63 / 3.48 | 10.98 / 11.18 | 9.23 / 9.44 | 15.01 / 15.17 | — |
| 24 | " | —NHN(CH$_3$)(C$_6$H$_5$) | 6 | 133–135 | 55.03 / 54.86 | 3.18 / 3.45 | 9.31 / 9.60 | 8.39 / 8.10 | 12.85 / 13.02 | — |
| 25 | " | —NHNHCH$_2$COOC$_2$H$_5$ | 7 | 99–100 | 47.63 / 47.06 | 3.14 / 3.48 | 9.50 / 9.68 | 8.05 / 8.17 | 13.04 / 13.14 | — |
| 26 | " | —NHNHP(=S)(OC$_2$H$_5$)(OC$_2$H$_5$) | 8 | 70–71 | 41.32 / 40.85 | 3.57 / 3.63 | 8.33 / 8.40 | 7.33 / 7.09 | 11.26 / 11.40 | 6.70 / 6.41 |
| 27 | " | —NHNHCHO | 9 | 176–177 | 44.62 / 44.75 | 2.33 / 2.41 | 11.21 / 11.18 | 9.49 / 9.44 | 15.23 / 15.17 | — |
| 28 | " | —NHNHCOCH$_3$ | 10 | 153–154 | 46.65 / 46.22 | 2.89 / 2.85 | 10.92 / 10.78 | 9.22 / 9.10 | 14.39 / 14.62 | — |
| 29 | " | —NHNHCOC$_2$H$_5$ | 11 | 148–149 | 47.98 / 47.59 | 3.12 / 3.24 | 9.92 / 10.40 | 8.51 / 8.78 | 14.21 / 14.12 | — |
| 30 | 3-Cl-4-CF$_3$C$_6$H$_3$ | —NHNHCOCH(CH$_3$)(CH$_3$) | 11 | 181–183 | 48.97 / 48.88 | 3.82 / 3.62 | 10.07 / 10.06 | 8.71 / 8.49 | 13.43 / 13.65 | — |

TABLE 2-continued

| Compound No. | Substituents in general formula I (A)ₙ/(B)ₘ | R | Synthesis method example No. | Melting point (°C.) (Infrared ray absorption spectra, cm⁻¹) | Elemental analysis value % (upper row, observed value; lower row, calculated value) C H N Cl F S |
|---|---|---|---|---|---|
| 31 | " | —NHNHC(=O)C(CH₃)₃ | 11 | 188–190 | 50.22 4.06 9.69 8.59 13.52 — / 50.06 3.97 9.73 8.21 13.20 |
| 32 | " | —NHNHC(=O)C₇H₁₅(n) | 11 | 103–105 | 53.21 4.85 8.77 7.73 11.99 — / 53.22 4.89 8.87 7.48 12.03 |
| 33 | " | —NHNHC(=O)CH=CHCH₃ | 10 | 170–171 | 49.98 3.13 9.24 8.74 13.50 — / 49.11 3.15 10.11 8.53 13.71 |
| 34 | " | —NHNHC(=O)—C₆H₅ | 11 | 72–73 | 54.01 2.61 8.92 7.81 11.77 — / 53.16 2.90 9.30 7.85 12.62 |
| 35 | " | —NHNHC(=O)—C₆H₃Cl₂ | 11 | 178–179 | 46.35 2.20 7.88 20.47 10.76 — / 46.13 2.13 8.07 20.43 10.95 |
| 36 | " | —NHNHC(=O)CH₂—C₆H₅ | 11 | 145–146 | 54.38 3.19 9.05 7.77 12.40 — / 54.14 3.25 9.02 7.61 12.24 |
| 37 | " | —NHNHC(=O)CH₂Cl | 11 | 188–188.5 | 42.64 2.34 9.83 17.14 14.03 — / 42.47 2.38 9.91 16.72 13.44 |
| 38 | " | —NHNHC(=O)CCl₃ | 11 | 173–174 | 36.94 1.75 8.64 27.66 11.64 — / 36.53 1.64 8.52 28.76 11.56 |
| 39 | " | —NHNHC(=O)CHClCH₃ | 11 | 151–152 | 44.26 2.33 9.32 16.34 13.18 — / 43.85 2.76 9.59 16.18 13.00 |
| 40 | " | —NHNHC(=O)CH₂O—C₆H₃Cl₂ | 11 | 164–165 | 46.68 2.59 7.55 19.00 9.98 — / 47.17 2.45 7.86 19.89 10.66 |
| 41 | " | —NHNHC(=O)CH=CHCOOH | 12 | 152–153 | 46.60 2.73 9.27 7.82 12.49 — / 45.81 2.49 9.43 7.95 12.79 |
| 42 | " | —NHNHC(=O)CH=CHCOOCH₃ | 12 | 165–166 | 47.02 2.59 8.78 7.50 13.14 — / 47.02 2.85 9.14 7.71 12.40 |
| 43 | " | —NHNHC(=O)CH₂CH₂COOCH₃ | 12 | 123–124 | 46.63 3.24 10.31 8.05 12.57 — / 46.81 3.27 9.10 7.68 12.34 |
| 44 | " | —NHNHC(=O)CH₂CH₂COOC₂H₅ | 12 | 117–118 | 47.90 3.11 8.55 7.54 12.03 — / 47.96 3.60 8.83 7.45 11.98 |
| 45 | " | —NHNHC(=O)CH₂CH₂COOCH(CH₃)₂ | 12 | 96–97 | 48.81 3.36 8.17 7.93 11.23 — / 49.04 3.91 8.58 7.24 11.64 |
| 46 | " | —NHNHC(=O)(CH₂)₃COOCH₃ | 12 | 121–123 | 48.13 3.17 8.40 7.40 11.81 — / 47.96 3.60 8.83 7.45 11.98 |
| 47 | " | —NHNHC(=O)C(=O)CH₃ | 11 | 210–212 | 46.28 2.18 9.96 9.26 13.60 — / 46.00 2.65 10.06 8.49 13.64 |
| 48 | " | —NHNHSO₂CH₃ | 13 | 206–207 | 40.15 2.50 9.56 8.33 13.54 7.57 / 39.49 2.60 9.87 8.33 13.39 7.53 |

TABLE 2-continued

| Compound No. | Substituents in general formula I (A)ₙ/(B)ₘ phenyl | R | Synthesis method example No. | Melting point (°C.) (Infrared ray absorption spectra, cm⁻¹) | C | H | N | Cl | F | S |
|---|---|---|---|---|---|---|---|---|---|---|
| 49 | " | —NHNHSO₂—C₆H₄—CH₃ | 13 | 146–147 | 47.89 / 47.86 | 2.91 / 3.01 | 8.01 / 8.37 | 7.44 / 7.06 | 11.30 / 11.36 | 6.73 / 6.3 |
| 50 | " | —NHNHSO₂—C₆H₄—NO₂ | 13 | 173–174 decomp. | 43.35 / 42.82 | 2.18 / 2.27 | 10.23 / 10.51 | 6.56 / 6.65 | 10.88 / 10.69 | 5.73 / 6.01 |
| 51 | " | —NHNHSO₂NHCH₃ | 13 | 182 decomp. | 38.40 / 38.14 | 2.16 / 2.74 | 12.41 / 12.71 | 8.14 / 8.04 | 12.75 / 12.93 | 7.54 / 7.24 |
| 52 | " | —NHNHCOCH₃ | 14 | 130–131 | 44.37 / 44.40 | 2.51 / 2.73 | 10.31 / 10.36 | 8.63 / 8.74 | 13.83 / 14.05 | — |
| 53 | " | —NHNHCOC₂H₅ | 14 | 118–119 | 42.72 / 42.92 | 2.89 / 3.12 | 9.92 / 10.01 | 8.36 / 8.45 | 13.59 / 13.58 | — |
| 54 | " | —NHNHCOC₄H₉(n) | 14 | 99–101 | 48.24 / 48.50 | 3.67 / 3.39 | 9.23 / 9.43 | 8.17 / 7.95 | 12.59 / 12.79 | — |
| 55 | " | —NHNHCOCH(CH₃)₂ | 14 | 115–116 | 46.22 / 47.07 | 3.43 / 3.49 | 9.48 / 9.69 | 8.58 / 8.17 | 13.33 / 13.14 | — |
| 56 | " | —NHNHCOCH₂CH(CH₃)₂ | 14 | 118–110 | 48.26 / 48.50 | 3.32 / 3.39 | 9.04 / 9.43 | 7.98 / 7.95 | 12.55 / 12.79 | — |
| 57 | " | —NHNHCO—C₆H₅ | 14 | 133–134.5 | 51.66 / 51.35 | 2.56 / 2.80 | 8.86 / 8.98 | 7.58 / 7.58 | 11.97 / 12.19 | — |
| 58 | " | —NHNHCSC₈H₁₇(n) | 15 | 83–84 | 50.60 / 50.81 | 4.92 / 4.86 | 8.00 / 8.08 | 6.90 / 6.82 | 10.80 / 10.96 | 6.17 / 6.17 |
| 59 | " | —NHNHCNHCH₃ | 16 | 167–168 | 44.59 / 44.51 | 2.91 / 2.99 | 13.89 / 13.84 | 8.70 / 8.76 | 14.04 / 14.08 | — |
| 60 | " | —NHNHCNHC₂H₅ | 16 | 184–185 | 45.82 / 45.89 | 3.32 / 3.37 | 13.27 / 13.38 | 8.38 / 8.47 | 13.50 / 13.61 | — |
| 61 | " | —NHNHCNHC₃H₇(n) | 16 | 183.5–184.5 | 47.76 / 47.18 | 3.50 / 3.73 | 12.91 / 12.95 | 8.12 / 8.19 | 12.97 / 13.17 | — |
| 62 | " | —NHNHCNHCH(CH₃)₂ | 16 | 195–195.5 | 47.33 / 47.18 | 3.54 / 3.73 | 13.01 / 12.95 | 8.76 / 8.19 | 13.01 / 13.17 | — |
| 63 | " | —NHNHCNHC₆H₁₃(n) | 16 | 144–145 | 50.70 / 50.58 | 4.35 / 4.67 | 11.65 / 11.80 | 7.41 / 7.47 | 11.83 / 12.00 | — |
| 64 | " | —NHNHCNH—C₆H₃Cl₂ | 16 | 186.5–188 | 44.39 / 44.84 | 1.83 / 2.26 | 10.33 / 10.46 | 20.07 / 19.86 | 10.48 / 10.64 | — |
| 65 | " | —NHNHCNH₂ (C=S) | 17 | 180.5–183 | 41.16 / 41.34 | 2.49 / 2.48 | 13.33 / 13.77 | 8.62 / 8.72 | 13.75 / 14.01 | 7.98 / 7.88 |

TABLE 2-continued

| Compound No. | (A)ₙ (B)ₘ | R | Synthesis method example No. | Melting point (°C.) (Infrared ray absorption spectra, cm⁻¹) | Elemental analysis value % (upper row, observed value; lower row, calculated value) | | | | | |
|---|---|---|---|---|---|---|---|---|---|---|
| | | | | | C | H | N | Cl | F | S |
| 66 | " | —NHNHC(=S)NHCH₃ | 18 | 160–161.5 | 45.18 / 42.81 | 3.37 / 2.88 | 12.93 / 13.32 | 8.84 / 8.43 | 13.32 / 13.55 | 7.36 / 7.62 |
| 67 | " | —NHNHC(=S)NHC₂H₅ | 18 | 180–181 | 44.21 / 44.19 | 2.68 / 3.24 | 12.90 / 12.88 | 7.91 / 8.15 | 13.05 / 13.10 | 7.76 / 7.37 |
| 68 | " | —NHNHC(=S)NHCH₂CH(CH₃)₂ | 18 | 197–198 | 46.79 / 46.70 | 4.12 / 3.92 | 12.10 / 12.10 | 8.27 / 7.66 | 12.19 / 12.31 | 7.14 / 6.93 |
| 69 | " | —NHNHC(=S)NHCH₂CH=CH₂ | 18 | 162–163 | 47.50 / 45.69 | 3.24 / 3.16 | 12.59 / 12.54 | 8.00 / 7.94 | 12.50 / 12.76 | 7.07 / 7.18 |
| 70 | " | —NHNHC(=S)NH—C₆H₁₁ | 18 | 151–152 | 49.68 / 49.13 | 4.05 / 4.12 | 11.73 / 11.46 | 7.68 / 7.25 | 11.39 / 11.66 | 6.92 / 6.56 |
| 71 | " | —NHN=C(CH₃)—CCl=CCl—C(=O)CH₃ (dichloro diketone hydrazone) | 19 | 149–150 | 41.28 / 41.11 | 1.51 / 1.42 | 8.46 / 8.46 | 20.67 / 21.40 | 12.56 / 11.47 | — |
| 72 | " | —NHN= (tetrahydro-benzo diketone hydrazone) | 19 | 157–159 | 51.88 / 52.13 | 2.55 / 3.54 | 8.68 / 8.68 | 7.82 / 7.33 | 11.58 / 11.78 | — |
| 73 | " | —NHN= (benzo diketone hydrazone) | 20 | 207–208 | 54.45 / 54.38 | 2.78 / 2.82 | 9.14 / 9.06 | 8.34 / 7.64 | 11.39 / 12.29 | — |
| 74 | " | —NHN=C(CH₃)(CH₂)₂C(=O)CH₃ | 19 | 168–171 | 47.40 / 47.51 | 2.56 / 2.58 | 9.88 / 9.78 | 8.28 / 8.25 | 13.05 / 13.26 | — |
| 75 | " | —NHN=C(CH₃)(CH₂)₃C(=O)CH₃ | 19 | 175–176 | 49.08 / 48.72 | 2.89 / 2.95 | 9.44 / 9.47 | 8.46 / 7.99 | 12.95 / 12.84 | — |
| 76 | " | —N(CH₃)—NH₂ | 21 | 96–97 | 46.49 / 46.48 | 3.00 / 3.06 | 10.79 / 11.62 | 9.26 / 9.80 | 15.28 / 15.76 | — |

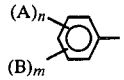

TABLE 2-continued

| Compound No. | Substituents in general formula I (A)$_n$ / (B)$_m$ | R | Synthesis method example No. | Melting point (°C.) (Infrared ray absorption spectra, cm$^{-1}$) | Elemental analysis value % (upper row, observed value; lower row, calculated value) | | | | | |
|---|---|---|---|---|---|---|---|---|---|---|
| | | | | | C | H | N | Cl | F | S |
| 77 | " | —N(CH$_3$)—NHCH$_3$ | 6 | (1605, 1527, 1315, 1265, 1167, 1127, 1080, 980) | 48.06 47.94 | 3.57 3.49 | 11.10 11.17 | 10.15 9.44 | 15.00 15.17 | — |
| 78 | " | —N(CH$_3$)—NHCH$_2$COOCH$_3$ | 7 | 73–74 | 47.24 47.07 | 3.38 3.49 | 9.18 9.69 | 8.37 8.17 | 13.01 13.14 | — |
| 79 | " | —N(CH$_3$)—NHCOCH$_3$ | 10 | 149–150 | 47.54 47.59 | 3.08 3.24 | 10.37 10.40 | 8.82 8.78 | 13.99 14.12 | — |
| 80 | " | —N(CH$_3$)—NHCOC$_2$H$_5$ | 11 | 168–169 | 49.12 48.87 | 3.45 3.63 | 10.18 10.06 | 8.61 8.48 | 13.74 13.64 | — |
| 81 | " | —N(CH$_3$)—NHCO—C$_6$H$_5$ | 11 | 160–161 | 53.93 54.14 | 3.24 3.25 | 8.57 9.02 | 7.36 7.61 | 12.00 12.24 | — |
| 82 | " | —N(CH$_3$)—NHCOCH$_2$Cl | 11 | 134–135 | 43.78 43.85 | 2.55 2.77 | 9.62 9.59 | 16.45 16.18 | 12.87 13.01 | — |
| 83 | " | —N(CH$_3$)—NHCOCCl$_3$ | 11 | 111.5–112.5 | 36.91 37.89 | 1.72 1.99 | 8.05 8.83 | 27.51 27.96 | 11.21 11.24 | — |
| 84 | " | —N(CH$_3$)—NHCOCH$_2$CH$_2$COOCH(CH$_3$)$_2$ | 12 | 96–97 | 49.93 50.06 | 5.00 4.20 | 8.74 8.34 | 7.52 7.04 | 10.97 11.31 | — |
| 85 | " | —N(CH$_3$)—NHSO$_2$CH$_3$ | 22 | 117–118 | 40.41 40.96 | 2.93 2.99 | 9.00 9.56 | 8.98 8.06 | 12.84 12.96 | 7.62 7.29 |
| 86 | " | —N(CH$_3$)—N(SO$_2$CH$_3$)$_2$ | 22 | 160–161.5 | 36.88 37.10 | 2.52 2.93 | 8.06 8.12 | 6.64 6.84 | 10.55 11.01 | 11.81 12.38 |
| 87 | " | —N(CH$_3$)—NHSO$_2$NHCH$_3$ | 23 | 124–126 | 38.71 39.61 | 2.81 3.11 | 11.92 12.32 | 7.37 7.79 | 12.38 12.53 | 7.01 7.05 |
| 88 | " | —N(CH$_3$)—NHCOCH$_3$ | 14 | 72.5–73.5 | 46.63 45.78 | 2.93 3.13 | 10.02 10.01 | 8.66 8.45 | 13.34 13.58 | — |
| 89 | " | —N(CH$_3$)—NHCOC$_2$H$_5$ | 14 | 103–105 | 46.91 47.07 | 3.19 3.49 | 9.61 9.69 | 8.54 8.17 | 13.35 13.14 | — |
| 90 | " | —N(CH$_3$)—NHCSC$_8$H$_{17}$(n) | 15 | 65–66 | 51.74 51.72 | 5.21 5.11 | 8.37 7.87 | 6.68 6.64 | 10.37 10.67 | 6.16 6.00 |
| 91 | " | —N(CH$_3$)—NHCONHCH$_3$ | 16 | 179–180.5 | 45.39 45.88 | 3.11 3.38 | 13.03 13.38 | 8.61 8.46 | 12.78 13.61 | — |
| 92 | " | —N(CH$_3$)—N(CONHCH$_3$)$_2$ | 26 | 47–48 | 45.90 45.43 | 3.49 3.61 | 14.59 14.72 | 6.99 7.45 | 11.59 11.98 | — |

TABLE 2-continued

| Compound No. | Substituents in general formula I (A)n/(B)m | R | Synthesis method example No. | Melting point (°C.) (Infrared ray absorption spectra, cm⁻¹) | Elemental analysis value % (upper row, observed value; lower row, calculated value) | | | | | |
|---|---|---|---|---|---|---|---|---|---|---|
| | | | | | C | H | N | Cl | F | S |
| 93 | " | CH₃ S<br>│ ‖<br>—N—NHCNHC₂H₅ | 18 | (2960, 1610,<br>1587, 1475<br>1322, 1263,<br>1125, 1080) | 45.56<br>45.48 | 3.47<br>3.60 | 11.92<br>12.48 | 8.08<br>7.90 | 13.02<br>12.70 | 7.52<br>7.14 |
| 94 | " | C₂H₅<br>│<br>—N—NH₂ | 5 | 87–88 | 48.14<br>47.94 | 3.23<br>3.49 | 11.15<br>11.19 | 9.41<br>9.44 | 15.00<br>15.17 | — |
| 95 | " | C₂H₅ O<br>│ ‖<br>—N—NHCCH₃ | 10 | 124–125 | 49.04<br>48.87 | 3.59<br>3.62 | 9.95<br>10.06 | 9.07<br>8.49 | 13.78<br>13.65 | — |
| 96 | " | C₂H₅ O<br>│ ‖<br>—N—NHCC₂H₅ | 11 | 165.5–167 | 50.70<br>50.06 | 4.04<br>3.97 | 9.61<br>9.74 | 8.28<br>7.98 | 13.01<br>13.20 | — |
| 97 | " | ·C₃H₇(n)<br>│<br>—N—NH₂ | 5 | (3380, 2980,<br>1612, 1525<br>1340, 1275,<br>1143, 1095) | 48.58<br>49.30 | 3.59<br>3.88 | 10.04<br>10.78 | 10.24<br>9.10 | 14.47<br>14.63 | — |
| 98 | " | C₄H₉(n)<br>│<br>—N—NH₂ | 5 | (3380, 2980,<br>1612, 1512<br>1340, 1275,<br>1145, 1095) | 50.92<br>50.56 | 3.86<br>4.24 | 10.25<br>10.41 | 8.69<br>8.78 | 13.97<br>14.12 | — |
| 99 | " | CH₂—C≡CH<br>│<br>—N—NH₂ | 5 | (3300, 2120,<br>1595, 1490<br>1325, 1270,<br>1130, 1082) | 50.03<br>49.81 | 2.78<br>2.87 | 10.54<br>10.90 | 9.48<br>9.19 | 14.57<br>14.78 | — |
| 100 | " | ⌬<br>│<br>—N—NH₂ | 5 | (3360, 1640,<br>1610, 1505<br>1335, 1270,<br>1140, 1090) | 53.87<br>53.84 | 3.04<br>3.09 | 10.12<br>9.92 | 8.39<br>8.67 | 13.62<br>13.45 | — |
| 101 | " | CO—⌬<br>│  CH₃<br>—N—N<br>    ⌬ | 11 | 178–179 | 60.29<br>59.00 | 3.09<br>3.37 | 7.06<br>7.37 | 6.24<br>6.22 | 9.86<br>10.00 | — |
| 102 | " | COCH₃  COCH₃<br>│   │<br>—N——N<br>        ＼COCH₃ | 24 | 106–107 | 48.51<br>48.07 | 3.07<br>3.18 | 8.24<br>8.85 | 6.86<br>7.48 | 11.56<br>12.00 | — |
| 103 | " | COOC₂H₅<br>│<br>—N—NHCOCH₃ | 25 | 134–135 | 46.91<br>46.81 | 3.47<br>3.27 | 9.54<br>9.09 | 8.49<br>7.68 | 12.18<br>12.34 | — |
| 104 | " | CONHC₂H₅<br>│<br>—N—NHCOCH₃ | 26 | (3300, 1723,<br>1490, 1323<br>1270, 1235,<br>1130, 1080) | 46.80<br>46.91 | 3.38<br>3.50 | 12.05<br>12.16 | 7.07<br>7.69 | 12.18<br>12.37 | — |
| 105 | " | COCH(Cl)CH₃<br>│<br>—N—NHCOCH(Cl)CH₃ | 20 | (3280, 3000,<br>1740, 1715<br>1595, 1490,<br>1250, 1090) | 43.72<br>43.14 | 3.06<br>2.86 | 7.50<br>7.94 | 20.21<br>20.12 | 10.46<br>10.78 | — |

TABLE 2-continued

| Compound No. | Substituents in general formula I (A)n (B)m | R | Synthesis method example No. | Melting point (°C.) (Infrared ray absorption spectra, cm$^{-1}$) | Elemental analysis value % (upper row, observed value; lower row, calculated value) | | | | | |
|---|---|---|---|---|---|---|---|---|---|---|
| | | | | | C | H | N | Cl | F | S |
| 106 | " | —N(CO-Ph)—NHCO-Ph | 20 | 167–168 | 58.18<br>58.33 | 2.48<br>3.08 | 7.49<br>7.56 | 6.69<br>6.38 | 10.13<br>10.25 | — |
| 107 | " | —N(CO-(2,4-Cl₂-Ph))—NHCO-(2,4,5-Cl₃-Ph) | 20 | 83–85 | 46.11<br>46.74 | 2.22<br>1.88 | 6.19<br>6.05 | 25.52<br>25.55 | 7.95<br>8.21 | — |
| 108 | " | —N(COOCH₃)—NHCOOCH₃ | 25 | 92–94 | 44.22<br>44.03 | 2.85<br>2.82 | 9.09<br>9.06 | 8.06<br>7.65 | 11.99<br>12.29 | — |
| 109 | " | —N(COOC₂H₅)—NHCOOC₂H₅ | 25 | (3380, 3000, 1812, 1780, 1507, 1340, 1280, 1095) | 45.72<br>46.39 | 2.89<br>3.48 | 8.04<br>8.54 | 7.15<br>7.21 | 10.92<br>11.59 | — |
| 110 | " | —N(COO-Ph)—NHCOO-Ph | 25 | 67–68 | 55.23<br>55.16 | 3.07<br>2.92 | 6.20<br>7.15 | 5.51<br>6.03 | 9.41<br>9.70 | — |
| 111 | " | —NHN=CHCH₃ | 27 | 153.5–156.5 | 48.05<br>48.20 | 2.73<br>2.97 | 11.31<br>11.24 | 10.01<br>9.49 | 14.98<br>15.25 | — |
| 112 | " | —NHN=CHCH(CH₃)₂ | 27 | 113.5–114.5 | 50.78<br>50.82 | 3.75<br>3.76 | 10.32<br>10.46 | 9.25<br>8.83 | 14.30<br>14.19 | — |
| 113 | " | —NHN=CHC₇H₁₅(n) | 27 | 93–94 | 54.99<br>55.08 | 4.97<br>5.06 | 9.34<br>9.18 | 8.20<br>7.74 | 12.60<br>12.45 | — |
| 114 | " | —NHN=CHCH=CH₂ | 27 | 167–167.5 | 49.83<br>49.82 | 2.80<br>2.88 | 10.76<br>10.89 | 9.47<br>9.19 | 14.97<br>14.78 | — |
| 115 | " | —NHN=CHCH=CHCH₃ | 27 | 177.5–179 | 50.97<br>51.07 | 3.12<br>3.28 | 10.30<br>10.51 | 9.01<br>8.87 | 14.41<br>14.26 | — |
| 116 | " | —NHN=CH-Ph | 27 | 202–203 | 55.20<br>55.12 | 3.13<br>3.01 | 9.54<br>9.64 | 8.96<br>8.14 | 12.99<br>13.08 | — |
| 117 | " | —NHN=CHCH=CH-Ph | 27 | 190.5–197 | 43.31<br>44.14 | 2.08<br>2.47 | 10.27<br>10.29 | 17.22<br>17.37 | 13.69<br>13.97 | — |
| 118 | " | —NHN=CHOCH₃ | 4 | 131–132 | 45.42<br>46.23 | 2.58<br>2.85 | 10.47<br>10.78 | 9.37<br>9.10 | 14.40<br>14.63 | — |
| 119 | " | —NHN=CHOC₂H₅ | 4 | 119–120 | 47.94<br>47.60 | 3.15<br>3.24 | 10.39<br>10.41 | 8.87<br>8.78 | 13.94<br>14.12 | — |
| 120 | " | —NHN=CHCH₂Cl | 27 | 115–117.5 | 43.31<br>44.14 | 2.08<br>2.47 | 10.27<br>10.29 | 17.22<br>17.37 | 13.69<br>13.97 | — |
| 121 | " | —NHN=CHCH₂CH(OH)CH₃ | 27 | 161–164 | 48.56<br>48.87 | 3.13<br>3.62 | 10.49<br>10.06 | 9.13<br>8.49 | 13.39<br>13.64 | — |
| 122 | " | —NHN=CH-(furan) | 27 | 207–208 | 57.15<br>57.21 | 3.01<br>3.27 | 9.26<br>9.10 | 8.07<br>7.68 | 12.53<br>12.34 | — |

TABLE 2-continued

| Compound No. | Substituents in general formula I (A)$_n$, (B)$_m$ | R | Synthesis method example No. | Melting point (°C.) (Infrared ray absorption spectra, cm$^{-1}$) | Elemental analysis value % (upper row, observed value; lower row, calculated value) | | | | | |
|---|---|---|---|---|---|---|---|---|---|---|
| | | | | | C | H | N | Cl | F | S |
| 123 | " | —NHN=C(CH$_3$)—Cl | 28 | 108–113 | 44.30 44.13 | 2.27 2.47 | 9.94 10.29 | 18.30 17.37 | 13.77 13.96 | — |
| 124 | " | —NHN=C(CH$_3$)—CH$_3$ | 29 | 134–135 | 49.23 49.56 | 3.26 3.38 | 10.77 10.84 | 9.50 9.14 | 14.00 14.70 | — |
| 125 | " | —NHN=C(CH$_3$)—C$_2$H$_5$ | 27 | 85–86 | 51.29 50.82 | 3.73 3.76 | 10.58 10.46 | 8.92 8.83 | 13.88 14.19 | — |
| 126 | " | —NHN=C(CH$_3$)—C$_9$H$_{19}$(n) | 27 | 62.5–63 | 57.24 57.65 | 5.83 5.85 | 8.26 8.40 | 7.09 7.09 | 11.21 11.40 | — |
| 127 | " | —NHN=C(CH$_3$)CH=CH$_2$ | 27 | 139–140 | 51.41 51.07 | 3.14 3.28 | 10.36 10.51 | 8.37 8.87 | 14.01 14.26 | — |
| 128 | " | —NHN=C(CH$_3$)—C$_6$H$_5$ | 27 | 178–180 | 56.44 56.07 | 3.20 3.36 | 9.83 9.34 | 7.88 7.88 | 12.79 12.67 | — |
| 129 | " | —NHN=C(CH$_3$)—OC$_2$H$_5$ | 4 | 94–116 | 49.07 48.87 | 3.41 3.62 | 10.14 10.06 | 8.78 8.49 | 13.40 13.64 | — |
| 130 | " | —NHN=C(CH$_3$)CH$_2$Cl | 27 | 177–178 | 45.69 45.51 | 2.79 2.87 | 9.88 9.95 | 16.86 16.80 | 13.27 13.50 | — |
| 131 | " | —NHN=C(CH$_3$)—CHCl$_2$ | 27 | 98–99 | 42.16 42.08 | 2.10 2.43 | 9.18 9.20 | 23.01 23.29 | 12.63 12.48 | — |
| 132 | " | —NHN=C(CH$_3$)—CH(OH)CH$_3$ | 27 | (3420, 3380, 1990, 1640, 1510, 1335, 1270, 1090) | 49.36 48.99 | 3.68 3.38 | 10.09 10.08 | 8.36 8.51 | 13.43 13.68 | — |
| 133 | " | —NHN=C(CH$_3$)CH$_2$CH$_2$COOH | 27 | 171–172 | 48.55 48.49 | 3.51 3.39 | 9.27 9.43 | 8.01 7.95 | 12.68 12.79 | — |
| 134 | " | —NHN=C(CH$_3$)—CH$_2$COOC$_2$H$_5$ | 27 | 125–126 | 49.50 49.63 | 3.40 3.73 | 9.14 9.14 | 7.34 7.71 | 12.68 12.40 | — |
| 135 | " | —NHN=C(C$_2$H$_5$)—C$_2$H$_5$ | 27 | 83–84.5 | 51.95 51.99 | 4.02 4.12 | 10.01 10.11 | 8.84 8.53 | 13.99 13.71 | — |
| 136 | " | —NHN=C(C$_2$H$_5$)—OC$_2$H$_5$ | 4 | 87–96 | 50.26 50.07 | 3.76 3.97 | 9.66 9.73 | 8.45 8.21 | 12.99 13.20 | — |
| 137 | " | —NHN=C(CH$_2$—CN)—C$_6$H$_5$ | 27 | 119–124 | 55.79 55.64 | 3.26 2.97 | 11.79 11.80 | 7.82 7.46 | 11.88 12.00 | — |
| 138 | " | —NHN=C(CH$_2$Cl)—CH$_2$Cl | 27 | 77.5–79 | 42.58 42.08 | 2.39 2.43 | 9.17 9.20 | 23.37 23.29 | 12.22 12.48 | — |
| 139 | " | —NHN=C(C$_6$H$_5$)$_2$ | 27 | 172–173 | 60.58 61.00 | 3.35 3.35 | 7.94 8.21 | 7.01 6.93 | 11.00 11.14 | — |

TABLE 2-continued

| Compound No. | Substituents in general formula I (A)$_n$ / (B)$_m$ | R | Synthesis method example No. | Melting point (°C.) (Infrared ray absorption spectra, cm$^{-1}$) | Elemental analysis value % (upper row, observed value; lower row, calculated value) | | | | | |
|---|---|---|---|---|---|---|---|---|---|---|
| | | | | | C | H | N | Cl | F | S |
| 140 | " | −NHN=C(SCH$_3$)(SCH$_3$) | 30 | 121–124 | 41.80 2.50 | 8.94 | 8.64 | 12.55 | 13.28 |
| | | | | | 42.52 2.46 | 9.30 | 7.84 | 12.61 | 14.19 |
| 141 | " | −NHN=⟨H⟩ (cyclohexyl) | 27 | 150–151 | 53.34 4.09 | 9.75 | 8.85 | 13.51 | — |
| | | | | | 53.34 4.01 | 9.82 | 8.29 | 13.32 | |
| 142 | " | −N(CH$_3$)−N=C(CH$_3$)(CH$_3$) | 29 | (1605, 1515, 1485, 1325, 1267, 1170, 1130, 1080) | 50.38 3.52 | 10.23 | 9.06 | 14.00 | — |
| | | | | | 50.81 3.77 | 10.46 | 8.86 | 14.19 | |
| 143 | Cl—⟨⟩— | −NHNHC(O)CH$_3$ | 3 | 153–155 | 52.67 3.75 | 12.50 | 11.32 | — | — |
| | | | | | 52.26 3.76 | 13.06 | 11.02 | | |
| 144 | CH$_3$—⟨⟩— | " | 3 | 115–118 | 59.51 4.75 | 13.69 | — | — | — |
| | | | | | 59.79 5.02 | 13.95 | | | |
| 145 | Cl,Cl—⟨⟩— | " | 3 | 179–180 | 47.65 3.10 | 11.54 | 19.57 | — | — |
| | | | | | 47.21 3.11 | 11.80 | 19.91 | | |
| 146 | CH$_3$,Cl—⟨⟩— | " | 3 | 106–107 | 54.24 3.84 | 11.57 | 10.73 | — | — |
| | | | | | 53.65 4.20 | 12.51 | 10.56 | | |
| 147 | Cl,Cl,F—⟨⟩— | " | 10 | 192–193 | 44.98 2.68 | 10.87 | 19.29 | 5.00 | — |
| | | | | | 44.94 2.69 | 11.23 | 18.95 | 5.08 | |
| 148 | Cl—⟨⟩— | −NHN=CHOCH$_3$ | 4 | 114–115 | 52.69 3.37 | 12.94 | 11.29 | — | — |
| | | | | | 52.26 3.76 | 13.06 | 11.02 | | |
| 149 | Cl,Cl—⟨⟩— | −NHNHC(O)CH$_2$OCH$_3$ | 11 | 154–155 | 47.06 3.34 | 11.20 | 18.63 | — | — |
| | | | | | 46.65 3.39 | 10.88 | 18.36 | | |
| 150 | " | −NHN(CH$_3$)(CH$_3$) | 6 | 72.5–74.5 | 49.28 3.96 | 12.04 | 19.98 | — | — |
| | | | | | 49.13 3.82 | 12.28 | 20.72 | | |
| 151 | " | −N(CH$_3$)−NH$_2$ | 21 | 111–112.5 | 47.43 3.06 | 12.15 | 21.30 | — | — |
| | | | | | 47.57 3.38 | 12.81 | 21.61 | | |
| 152 | " | −N(CH$_3$)−NHCOCH$_3$ | 10 | 140–142 | 48.57 3.42 | 10.83 | 19.48 | — | — |
| | | | | | 48.66 3.54 | 11.35 | 19.15 | | |
| 153 | " | −N(CH$_3$)−NHCOC$_2$H$_5$ | 11 | 152.5–154.5 | 50.24 3.84 | 10.36 | 18.62 | — | — |
| | | | | | 50.01 3.94 | 10.94 | 18.45 | | |

TABLE 2-continued

| Compound No. | Substituents in general formula I (A)$_n$/(B)$_m$ phenyl | R | Synthesis method example No. | Melting point (°C.) (Infrared ray absorption spectra, cm$^{-1}$) | C | H | N | Cl | F | S |
|---|---|---|---|---|---|---|---|---|---|---|
| 154 | 2,4-Cl, 5-Cl (dichloro) | $-\underset{CH_3}{N}-N\underset{O}{\overset{O}{\diagup}}(CH_2)_2$ (succinimide-type) | 19 | 90–92 | 49.24 / 49.77 | 3.51 / 3.20 | 10.34 / 10.25 | 17.92 / 17.29 | — | — |
| 155 | CF$_3$, Cl | —NHNHCCH$_2$OCH$_3$ (C=O) | 11 | 112–114 | 46.21 / 45.78 | 3.08 / 3.12 | 9.73 / 10.01 | 9.31 / 8.45 | 13.39 / 13.58 | — |
| 156 | " | —NHNHC—COC$_2$H$_5$ (O,O) | 11 | (3330, 1705, 1615, 1485, 1320, 1260, 1125, 1075) | 50.08 / 50.82 | 3.72 / 3.26 | 7.21 / 6.97 | 8.54 / 8.83 | 14.77 / 14.19 | — |
| 157 | " | —NHNHC(CH$_2$)$_4$COOCH$_3$ | 12 | 127–128 | 48.82 / 49.04 | 3.26 / 3.91 | 7.64 / 8.58 | 7.55 / 7.24 | 11.70 / 11.64 | — |
| 158 | " | —NH—N (maleimide) | 19 | 147–148 | 48.51 / 47.73 | 2.63 / 2.16 | 8.94 / 9.82 | 8.12 / 8.29 | 13.24 / 13.33 | — |
| 159 | " | —NHN (CH$_2$)$_4$ (glutarimide) | 19 | 167–168 | 50.62 / 49.84 | 3.59 / 3.30 | 9.49 / 9.18 | 8.34 / 7.75 | 12.69 / 12.45 | — |
| 160 | " | —NHNHC(CH$_2$)$_2$COOH | 11 | 169–170 | 45.83 / 45.60 | 2.30 / 2.93 | 9.36 / 9.38 | 7.45 / 7.92 | 12.74 / 12.73 | — |
| 161 | " | $-\underset{COCH_3}{N}-NHCOCH_3$ | 24 | (3310, 1675, 1580, 1525, 1320, 1260, 1125, 1080) | 47.01 / 47.29 | 3.21 / 3.03 | 10.02 / 9.73 | 8.31 / 8.21 | 13.51 / 13.20 | — |
| 162 | " | $-\underset{CH_3}{N}-NHC(CH_2)_3COOH$ | 11 | 101–103 | 47.34 / 47.96 | 3.51 / 3.60 | 8.56 / 8.83 | 7.71 / 7.45 | 11.70 / 11.98 | — |
| 163 | " | $-\underset{C_3H_7(n)}{N}-NHCOCH_3$ | 10 | 143–145 | 50.19 / 50.06 | 3.91 / 3.97 | 9.63 / 9.74 | 8.34 / 8.21 | 12.99 / 13.20 | — |
| 164 | " | $-\underset{C_3H_7(n)}{N}-NHCOC_2H_5$ | 11 | 132–135 | 51.62 / 51.18 | 4.37 / 4.30 | 9.44 / 9.43 | 8.00 / 7.95 | 12.57 / 12.79 | — |
| 165 | " | $-\underset{CH_3}{N}-NHC(CH_2)_2COOH$ | 12 | 126–128 | 47.02 / 46.81 | 3.31 / 3.27 | 9.08 / 9.10 | 7.82 / 7.68 | 11.98 / 12.34 | — |
| 166 | " | $-\underset{CH_3}{N}-NHC(CH_2)_2COOCH_3$ | 12 | 92–93 | 47.91 / 47.96 | 3.66 / 3.60 | 8.72 / 8.83 | 7.44 / 7.45 | 11.78 / 11.98 | — |
| 167 | " | $-\underset{CH_3}{N}-NHC(CH_2)_3COOCH_3$ | 12 | 90–91 | 49.13 / 49.04 | 3.92 / 3.91 | 8.42 / 8.58 | 7.33 / 7.24 | 11.50 / 11.64 | — |

TABLE 2-continued

| Compound No. | Substituents in general formula I (A)$_n$ / (B)$_m$ | R | Synthesis method example No. | Melting point (°C.) (Infrared ray absorption spectra, cm$^{-1}$) | Elemental analysis value % (upper row, observed value; lower row, calculated value) | | | | | |
|---|---|---|---|---|---|---|---|---|---|---|
| | | | | | C | H | N | Cl | F | S |
| 168 | " | −NH−N=C(Cl)−C(CH$_3$)$_3$ | 28 | 101–102 | 47.99 48.01 | 3.93 3.58 | 9.25 9.33 | 16.36 15.75 | 12.85 12.66 | — |
| 169 | " | −NH−NHC(O)−C(O)OCH$_3$ | 11 | (1670 / 1765) | 44.14 44.30 | 2.42 2.55 | 9.96 9.68 | 7.70 8.17 | 13.29 13.14 | — |
| 170 | " | −NH−NHC(O)(CH$_2$)$_4$C(O)NH−NH−[2-Cl-4-(F$_3$C)C$_6$H$_3$-O-2-NO$_2$-C$_6$H$_3$] | 31 | 201–202 | 48.16 48.71 | 3.24 2.95 | 9.96 9.47 | 7.74 7.99 | 12.93 12.84 | — |
| 171 | " | −NH−NHC(O)C(O)NH−NH−[2-Cl-4-(F$_3$C)C$_6$H$_3$-O-2-NO$_2$-C$_6$H$_3$] | 31 | 266–268 (decomp.) | 44.39 44.87 | 2.41 2.15 | 11.65 11.21 | 9.18 9.46 | 15.55 15.21 | — |
| 172 | " | −NH−NHCONH−NH−[2-Cl-4-(F$_3$C)C$_6$H$_3$-O-2-NO$_2$-C$_6$H$_3$] | 31 | 233–234 | 44.69 44.95 | 2.47 2.24 | 11.22 11.65 | 9.36 9.83 | 16.03 15.80 | — |
| 173 | " | −NH−N(CH$_3$)(COCH$_3$) | 32 | 101.5–102.5 | 47.59 47.32 | 3.30 3.01 | 10.41 10.36 | 8.78 9.48 | 14.12 14.11 | — |
| 174 | " | −NH−N(C$_2$H$_5$)(COCH$_3$) | 32 | (1670 / 3280) | 48.87 48.52 | 3.63 3.66 | 10.06 10.11 | 8.48 8.72 | 13.64 13.57 | — |
| 175 | 2-Cl-4-(F$_3$C) | −N(C$_2$H$_5$)−NHC(O)(CH$_2$)$_2$C(O)OC$_2$H$_5$ | 12 | 77–78 | 50.34 50.06 | 3.98 4.20 | 8.43 8.34 | 7.22 7.04 | 11.06 11.31 | — |
| 176 | " | −N(C$_2$H$_5$)−NHCOOC$_2$H$_5$ | 14 | 90–92 | 48.78 48.27 | 3.73 3.83 | 9.46 9.38 | 8.19 7.92 | 12.56 12.73 | — |
| 177 | " | −N(CH$_3$)−N(CH$_3$)−C(O)(CH$_2$)$_2$C(O)OC$_3$H$_7$(i) | 12 | (1720) | 51.23 51.01 | 4.12 4.47 | 8.50 8.11 | 6.81 6.84 | 11.19 11.00 | — |
| 178 | 2,4-Cl$_2$-5-F | −N(CH$_3$)−NHCOCH$_3$ | 10 | 160–162 | 46.77 46.40 | 3.45 3.11 | 10.38 10.82 | 17.98 18.26 | 4.67 4.89 | — |
| 179 | " | −N(CH$_3$)−NH$_2$ | 21 | 116–118 | 45.56 45.10 | 2.62 2.91 | 12.44 12.13 | 20.31 20.48 | 5.08 5.49 | — |
| 180 | " | −N(C$_2$H$_5$)−NH$_2$ | 21 | 139–140 | 46.93 46.68 | 3.03 3.36 | 11.74 11.67 | 19.95 19.69 | 5.06 5.27 | — |
| 181 | " | −N(C$_3$H$_7$(n))−NHCOCH$_3$ | 10 | 160–161 | 49.06 49.05 | 3.76 3.88 | 10.09 10.10 | 17.29 17.04 | 4.59 4.57 | — |

TABLE 2-continued

| Compound No. | Substituents in general formula I (A)$_n$/(B)$_m$ phenyl | R | Synthesis method example No. | Melting point (°C.) (Infrared ray absorption spectra, cm$^{-1}$) | C | H | N | Cl | F | S |
|---|---|---|---|---|---|---|---|---|---|---|
| 182 | " | $\begin{array}{c}C_3H_7(n)\\|\\-N-NHCOC_2H_5\end{array}$ | 11 | 168–169 | 50.56 / 50.24 | 3.97 / 4.22 | 9.84 / 9.77 | 16.35 / 16.48 | 4.36 / 4.42 | — |
| 183 | " | $\begin{array}{c}C_3H_7(n)\;\;O\;\;\;\;O\\|\;\;\;\;\;\;\;\;\;\|\;\;\;\;\;\;\|\\-N-NHC(CH_2)_2COC_3H_7(i)\end{array}$ | 12 | (1740) | 51.39 / 51.17 | 4.37 / 4.69 | 7.79 / 8.14 | 13.53 / 13.73 | 3.58 / 3.68 | — |
| 184 | " | $-NHN\begin{array}{c}C_2H_5\\ \\COCH_3\end{array}$ | 32 | 142.5–143.5 | 47.52 / 47.77 | 3.40 / 3.51 | 10.60 / 10.45 | 18.01 / 17.63 | 4.70 / 4.72 | — |
| 185 | " | $\begin{array}{c}C_2H_5\\|\\-N-NHCOCH_3\end{array}$ | 10 | 161–162 | 48.28 / 47.78 | 3.01 / 3.50 | 10.66 / 10.45 | 17.76 / 17.63 | 4.72 / 4.72 | — |
| 186 | " | $\begin{array}{c}C_2H_5\\|\\-N-NHCOC_2H_5\end{array}$ | 11 | 184.5–185.5 | 49.61 / 49.05 | 3.44 / 3.87 | 10.27 / 10.09 | 17.07 / 17.03 | 4.51 / 4.56 | — |
| 187 | " | $\begin{array}{c}C_2H_5\;\;O\;\;\;\;O\\|\;\;\;\;\;\;\|\;\;\;\;\;\;\|\\-N-NHC(CH_2)_2COC_3H_7(i)\end{array}$ | 12 | (1680 / 1730) | 50.00 / 50.21 | 4.38 / 4.41 | 7.96 / 8.36 | 13.87 / 14.11 | 3.47 / 3.78 | — |
| 188 | 2,3,4-Cl$_3$-phenyl | $\begin{array}{c}C_2H_5\\|\\-N-NH_2\end{array}$ | 21 | 154–155 | 44.17 / 44.64 | 3.03 / 3.21 | 10.77 / 11.17 | 28.60 / 28.24 | — | — |
| 189 | " | $\begin{array}{c}CH_3\\|\\-N-NH_2\end{array}$ | 21 | 143–146 | 43.25 / 43.06 | 2.99 / 2.78 | 11.55 / 11.60 | 29.52 / 29.33 | — | — |
| 190 | " | $\begin{array}{c}CH_3\\|\\-N-NHCOCH_3\end{array}$ | 10 | 158–160 | 44.35 / 44.52 | 2.75 / 2.99 | 10.30 / 10.39 | 26.02 / 26.29 | — | — |
| 191 | " | $\begin{array}{c}C_3H_7(n)\\|\\-N-NHCOCH_3\end{array}$ | 10 | 185–186 | 47.26 / 47.18 | 3.63 / 3.73 | 9.91 / 9.71 | 23.95 / 24.58 | — | — |
| 192 | " | $\begin{array}{c}C_3H_7(n)\;\;O\;\;\;\;O\\|\;\;\;\;\;\;\;\;\;\|\;\;\;\;\;\;\|\\-N-NHC(CH_2)_2COC_3H_7(i)\end{array}$ | 12 | (1730) | 49.41 / 49.59 | 4.72 / 4.54 | 7.83 / 7.89 | 19.97 / 19.96 | — | — |
| 193 | " | $-NHN\begin{array}{c}C_2H_5\\ \\COCH_3\end{array}$ | 32 | 153–155 | 45.98 / 45.90 | 3.20 / 3.37 | 10.11 / 10.04 | 25.77 / 25.41 | — | — |
| 194 | " | $\begin{array}{c}CH_3\;\;O\;\;\;\;O\\|\;\;\;\;\;\|\;\;\;\;\;\;\|\\-N-NHC(CH_2)_2COC_3H_7(i)\end{array}$ | 12 | 120–121 | 47.99 / 47.59 | 4.14 / 3.99 | 8.45 / 8.33 | 21.26 / 21.07 | — | — |
| 195 | " | $\begin{array}{c}C_2H_5\;\;O\;\;\;\;O\\|\;\;\;\;\;\|\;\;\;\;\;\;\|\\-N-NHC(CH_2)_2COC_3H_7(i)\end{array}$ | 12 | (1680 / 1730) | 49.42 / 48.61 | 4.27 / 4.26 | 7.72 / 8.10 | 19.59 / 20.50 | — | — |
| 196 | " | $\begin{array}{c}C_2H_5\\|\\-N-NHCOCH_3\end{array}$ | 10 | 184–185 | 45.62 / 45.90 | 2.81 / 3.37 | 9.82 / 10.03 | 25.61 / 25.40 | — | — |
| 197 | " | $\begin{array}{c}C_2H_5\;\;O\;\;\;\;O\\|\;\;\;\;\;\|\;\;\;\;\;\;\|\\-N-NHC(CH_2)_2COC_2H_5\end{array}$ | 12 | 1730 | 48.48 / 47.59 | 3.70 / 3.99 | 7.49 / 8.32 | 20.19 / 21.07 | — | — |
| 198 | F$_3$C-phenyl | —NHNHCOCH$_3$ | 10 | 150–151 | 51.03 / 50.70 | 3.72 / 3.40 | 11.56 / 11.82 | — | 16.16 / 16.04 | — |

TABLE 2-continued

| Compound No. | Substituents in general formula I (A)$_n$-⌬-(B)$_m$ | R | Synthesis method example No. | Melting point (°C.) (Infrared ray absorption spectra, cm$^{-1}$) | Elemental analysis value % (upper row, observed value; lower row, calculated value) | | | | | |
|---|---|---|---|---|---|---|---|---|---|---|
| | | | | | C | H | N | Cl | F | S |
| 199 | " | —NHNHCOOC$_2$H$_5$ | 14 | 99.5–100 | 50.14 49.87 | 3.58 3.66 | 11.08 10.91 | — | 14.35 14.79 | — |
| 200 | " | —NHNHCOCH$_2$Cl | 11 | 171–172 | 45.89 46.22 | 3.17 2.84 | 10.42 10.78 | 9.51 9.09 | 14.54 14.62 | — |
| 201 | " | —NHN=C(CH$_3$)(CH$_3$) | 29 | 120–120.5 | 54.26 54.39 | 4.23 3.99 | 11.35 11.89 | — | 16.01 16.13 | — |
| 202 | " | —NHN(succinimide) | 19 | 166–167 | 52.21 51.65 | 3.30 3.06 | 10.02 10.63 | — | 13.94 14.42 | — |
| 203 | " | —N(CH$_3$)NHCOCH$_3$ | 10 | 159.5–160.5 | 51.78 52.03 | 4.15 3.82 | 11.38 11.38 | — | 15.11 15.43 | — |
| 204 | " | —NHN(C$_2$H$_5$)(COCH$_3$) | 32 | (3350, 1680) | 54.07 53.26 | 4.16 4.21 | 11.20 10.96 | — | 15.17 14.87 | — |
| 205 | " | —NHNH—CO—CO—NHNH— (with F$_3$C-⌬-O-⌬-NO$_2$) | 31 | 249 decomp. | 50.25 49.42 | 3.12 2.66 | 11.89 12.35 | — | 16.12 16.75 | — |
| 206 | " | —NHNHCOCH$_2$CH$_2$COOH | 12 | 173.5–174.5 | 51.38 51.39 | 3.87 3.55 | 10.61 10.57 | — | 14.29 14.35 | — |
| 207 | " | —NHNHCOCH$_2$CH$_2$COOC$_2$H$_5$ | 12 | 97–98 | 51.39 51.70 | 4.12 4.11 | 9.45 9.52 | — | 13.10 12.91 | — |
| 208 | " | —N(CH$_3$)NHCOCH$_2$CH$_2$COOC$_2$H$_5$ | 12 | 73–74 | 52.12 52.75 | 4.59 4.43 | 9.04 9.23 | — | 12.43 12.52 | — |

When the compounds of the present invention are used as herbicide, the amount of the agent used is 2–50 g, preferably 5–20 g, per are for paddy field, and 5–50 g, preferably 5–20 g for dry field crops, although the amount is affected by soil to a certain extent in the case of the soil treatment prior to occurrence of weeds. As for the treating method, pre-plant soil incorporation, treatment of soil, treatment of filled water, treatment of stems and leaves as well as soil, etc. are possible, but the treating method is not limited to these treatments.

In the practical use of the compounds of the present invention, they can be used in the form of such formulations as dust, granule, wettable powder, emulsion, etc., but the using manner is not limited to these formulations.

The compounds of the present invention can be applied directly or indirectly to plants to be controlled, as a herbicidal composition containing a generally employed carrier or as a component in formulations.

The generally employed carrier referred to means any of substances which can be employed for dissolving, dispersing or diffusing herbicidal compounds without harming their effectiveness and which themselves have no harmful function upon soil, facilities, equipments employed and crops. For example, minerals such as bentonite, clay, montmorillonite, etc., natural substances such as cellulose, thawdust, starch, etc., resins such as polyvinyl chloride, etc. and organic solvents such as benzene, acetone, alcohols, esters e.g. ethyl acetate, are mentioned.

As for the surfactant employed for the purpose of emulsification, dispersion, etc., any of nonionic, anionic, cationic and amphoteric surfactants can be employed. For example, polyethylene glycol, sorbitan oleic acid monoester, sodium dodecylbenzenesulfonate, lauryltrimethylammonium chloride, stearyldimethylbetaine, etc. are mentioned.

The content of the compounds expressed by the above-mentioned general formula I, in the herbicides of the present invention is preferred to be 2–10% for granules, 40–80% for wettable powder, 10–50% for emulsion and 1–5% for dusts.

The formulation examples of the compounds of the present invention are shown below, but the present invention is not limited thereto.

In the formulation examples, the active ingredient compounds of the general formula I are expressed by the compound No. in Table 2, and "part" refers to "part by weight".

FORMULATION EXAMPLE 1

A compound (6 parts, compound No. 78), bentonite (70 parts), talc (21 parts), sodium dodecylbenzene-sulfonate (2 parts) and sodium ligninsulfonate (one part) are mixed together, and a proper amount of water is added. After kneading, granulation is carried out in a usual manner by means of an extruding granulator to obtain 100 parts of granules.

FORMULATION EXAMPLE 2

A compound (50 parts, compound No. 28), diatomaceous earth (40 parts) and sodium dodecylbenzene-sulfonate (10 parts) are mixed and milled to obtain 100 parts of a wettable powder.

FORMULATION EXAMPLE 3

A compound (10 parts, compound No. 75), Solpol 800A (an emulsifier made by Toho Kagaku Co., Japan) (10 parts) and benzene (80 parts) are mixed together to obtain 100 parts of an emulsion.

FORMULATION EXAMPLE 4

A compound (60 parts, compound No. 44), talc (30 parts), sodium laurylphosphate (7 parts) and sodium alkylnaphthalenesulfonate (3 parts) are mixed togther to obtain 100 parts of a wettable powder.

FORMULATION EXAMPLE 5

A compound (5 parts, compound No. 79), bentonite (73 parts), talc (20 parts), polyoxyethylene glycol monolaurate (one part) and sodium naphthalenesulfonate (one part) are mixed together, and a proper amount of water is then added. After kneading, granulation is carried out in a usual manner by means of an extruding granulator to obtain 100 parts of granules.

FORMULATION EXAMPLE 6

A compound (3 parts, compound No. 121) and clay (97 parts) are mill-mixed to obtain 100 parts of dust.

When the compounds of the present invention are used as a hericide, it is, of course, possible to use them in admixture with one kind or more of other herbicides, pesticides such as insecticides, germicides, plant growth regulators, etc., soil conditioners or fertilizable substances, and it is also possible to formulate them in admixture with the foregoing materials. Further, in some cases, a synergistic effect can be expected.

For example, representative examples of the herbicides employed at the same time with the herbicides of the present invention include the following compounds, but they are not limited to these compounds:

AUXIN HERBICIDES 2,4-dichlorophenoxyacetic acid (including its esters and salts),
2-methyl-4-chlorophenoxyacetic acid (including its esters and salts),
4-(2,4-dichlorophenoxy)butyric acid (including its esters and salts),
3-amino-2,5-dichlorobenzoic acid,
4-chloro-2-oxobenzothiazolin-3-ylacetic acid,

TRIAZINE HERBICIDES 3-chloro-4,6-bis(ethylamino)-1,3,5-triazine,
2,4-bis(ethylamino)-6-methylthio-1,3,5-triazine,
2-chloro-4-ethylamino-6-isopropylamino-1,3,5-triazine,
2-ethylamino-4-isopropylamino-6-methylthio-1,3,5-triazine,
2-chloro-4-diethylamino-6-ethylamino-1,3,5-triazine,

UREA HERBICIDES 3-(3,4-dichlorophenyl)-1,1-diethylurea,
3-(3,4-dichlorophenyl)-1-methoxy-1-methylurea,
1,1-dimethyl-3-(3-trifluoromethylphenyl)urea,
1-(2-methylcyclohexyl)-3-phenylurea,
3-(4-chlorophenyl)-1-methoxy-1-methylurea,
3-[4-(4-chlorophenoxy)phenyl]-1,1-dimethylurea,
3-[4-(4-methoxyphenoxy)phenyl]-1,1-dimethylurea,

ACID ANILIDE HERBICIDES

3',4'-dichloropropionanilide,
2-methyl-4-chlorophenoxyaceto-O-chloroanilide,
α-chloro-N-isopropylacetanilide,
5-chloro-4-methyl-2-propionanilido-1,3-thiazole,
2-chloro-(2',6'-dinitroanilino)-N-methylpropionamide,
2-chloro-2',6'-diethyl-N-(butoxymethyl)acetanilide,
2-chloro-2',6'-diethyl-N-(propoxyethyl)acetanilide,
2-chloro-N-isopropylacetanilide,

HYDROXYBENZONITRILE HERBICIDES 4-hydroxy-3,5-diiodobenzonitrile,
3,5-dibromo-4-hydroxybenzonitrile,
4-hydroxy-3,5-diiodobenzonitrile octanoate,

URACIL HERBICIDES 3-tert-butyl-5-chloro-6-methyluracil,
5-bromo-3-sec-butyl-6-methyluracil,
3-cyclohexyl-5,6-trimethyleneuracil,

DIPHENYL ETHER HERBICIDES 2,4-dichloro-4'-nitrodiphenyl ether,
2,4,6-trichloro-4'-nitrodiphenyl ether,
2,4-dichloro-3'-methoxy-4'-nitrodiphenyl ether,
2-nitro-4-trifluoromethyl-4'-nitrodiphenyl ether,
2-chloro-4-trifluoromethyl-4'-nitrodiphenyl ether,
2-chloro-4-trifluoromethyl-3'-methoxycarbonyl-4'-nitrodiphenyl ether,
methyl(±)-2-[4-(2,4-dichlorophenoxy)phenoxy]propionate,

CARBAMIC ACID HERBICIDES isopropyl-N-phenylcarbamate,
isopropyl-N-(3-chlorophenyl)carbamate,
methyl-N-(3,4-dichlorophenyl)carbamate,
S-ethyldipropylthiocarbamate,
S-p-chlorobenzyldiethylthiocarbamate,
methyl-N-(4-amino-benzenesulfonyl)carbamate,
ethyl-N,N-di-n-propylthiocarbamate,
4-chlorobenzyl-N,N-diethylthiocarbamate,
ethyl-N,N-hexamethylenethiocarbamate,

ANILINE HERBICIDES 2,6-dinitro-N,N-dipropyl-4-trifluoromethylaniline,
N-butyl-N-ethyl-2,6-dinitro-4-trifluoromethylaniline,
3,4-dimethyl-2,6-dinitro-N-1-ethylpropylaniline,

PYRIDINIUM SALT HERBICIDES 1,1'-dimethyl-4,4'-bispyridinium dichloride,
9,10-dihydroxy-8a,10a-diazoniaphenanthrone dibromide,

OTHER HERBICIDES

N,N-bis(phosphonomethyl)glycine,
α,α,α-trifluoro-2,6-dinitro-N,N-dipropyl-p-toluidine, S-(2-methyl-1-pyperidylcarbonylmethyl)-o,o-dipropylphosphorodithioate,
4-amino-6-tert-butyl-3-methylthio-1,2,4-triazin-5-one,
o-ethyl-o-(2-nitro-5-methylphenyl)-N-secbutylphosphoroamidothioate,
N-(o,o-dipropyldithiophosphorylacetyl)-2-methylpyperidine,
2,4-diamino-5-methylthio-6-chloropyrimidine, The herbicidal activity of the compounds of the present invention will be illustrated by way of Test examples.

TEST EXAMPLE 1

Test for controlling weeds for dry field crops according to the soil treatment prior to germination.

An air-dried soil of dry field (passed through a 14 mesh sieve) (10 Kg) was put in a pot made of resin (a/1000), and a compound fertilizer (N, $P_2O_5$ and $K_2O$, each 1 g) was applied to the whole layer of the soil, followed by making the water content of the soil 60% of the maximum water-holding capacity. The soil was seeded with a fixed amount of seeds of a crop to be tested, or weeds, and covered with soil. A liquid obtained by diluting a fixed amount of an emulsion prepared from a compound to be tested, according to Formulation example 3, with water in an amount corresponding to 10 l per are, was sprayed onto the soil by means of a slight pressure sprayer.

The resulting pot was placed in a greenhouse and water administration was always carried out to grow the plant. Thirty days after the spray of the agent, the occurrence or growth condition of weeds and crops was investigated to obtain the results shown in Table 3.

In this Table, the phytotoxicity extent upon crops and the herbicidal effect upon weeds, were expressed according to the evaluation standards mentioned below, in comparison of the occurrence or growth condition of weeds or crops, with the air-dried weight of weeds or crops in untreated section.

The compounds to be tested were shown by the compound No. of Table 2 (this applies to the Test examples mentioned below). Among the compounds to be tested, of Table 3, compounds Nos. 11, 13, 15, 16, 24, 117, 186 and 191 could completely control the following weeds in an amount of agent used, of 10 g/a, and others could control them in an amount of agent used, of 5 g/a:

Foxtail, Bluegrass, Foxtailgrass, Johnsongrass, Bermudagrass, Quackgrass, Smartweed, Velvetleaf, Morningglory, Hertleaf cocklebur, *Rumex japonicus*, Wild mustard, Shepherdspurse, etc.

Evaluation standards:

| | |
|---|---|
| 0: Percentage of existence of weeds or crops indicated by the air-dried weight ratio relative to weeds or crops in untreated section | 76–100% |
| 1: Percentage of existence of weeds or crops indicated by the air-dried weight ratio relative to weeds or crops in untreated section | 51–75% |
| 2: Percentage of existence of weeds or crops indicated by the air-dried weight ratio relative to weeds or crops in untreated section | 36–50% |
| 3: Percentage of existence of weeds or crops indicated by the air-dried weight ratio relative to weeds or crops in untreated section | 11–35% |
| 4: Percentage of existence of weeds or crops indicated by the air-dried weight ratio relative to weeds or crops in untreated section | 6–10% |
| 5: Percentage of existence of weeds or crops indicated by the air-dried weight ratio relative to weeds or crops in untreated section | 0–5% |

TABLE 3

| Tested compound No. | Amount of active ingredient used, g/a | Weeds Crabgrass | Barnyardgrass | Redroot pigweed | Lambsquarters | Crops Soybean | Cotton |
|---|---|---|---|---|---|---|---|
| 8 | 5 | 5 | 5 | 5 | 5 | 0 | 0 |
|  | 10 | 5 | 5 | 5 | 5 | 0 | 0 |
| 11 | 5 | 5 | 4 | 4 | 5 | 0 | 0 |
|  | 10 | 5 | 5 | 5 | 5 | 0 | 0 |
| 13 | 5 | 5 | 5 | 4 | 5 | 0 | 0 |
|  | 10 | 5 | 5 | 5 | 5 | 0 | 0 |
| 15 | 5 | 5 | 4 | 4 | 4 | 0 | 0 |
|  | 10 | 5 | 5 | 5 | 5 | 0 | 0 |
| 16 | 5 | 5 | 5 | 4 | 4 | 0 | 0 |
|  | 10 | 5 | 5 | 5 | 5 | 0 | 0 |
| 19 | 5 | 5 | 5 | 5 | 5 | 0 | 0 |
|  | 10 | 5 | 5 | 5 | 5 | 0 | 0 |
| 20 | 5 | 5 | 5 | 5 | 5 | 0 | 0 |
|  | 10 | 5 | 5 | 5 | 5 | 0 | 0 |
| 22 | 5 | 5 | 5 | 4 | 4 | 0 | 0 |
|  | 10 | 5 | 5 | 5 | 5 | 0 | 0 |
| 23 | 5 | 5 | 5 | 5 | 5 | 0 | 0 |
|  | 10 | 5 | 5 | 5 | 5 | 0 | 0 |
| 24 | 5 | 4 | 4 | 5 | 5 | 0 | 0 |
|  | 10 | 5 | 5 | 5 | 5 | 0 | 0 |
| 27 | 5 | 5 | 5 | 5 | 5 | 0 | 0 |
|  | 10 | 5 | 5 | 5 | 5 | 0 | 0 |
| 28 | 5 | 5 | 5 | 5 | 5 | 0 | 0 |
|  | 10 | 5 | 5 | 5 | 5 | 0 | 0 |
| 29 | 5 | 5 | 5 | 5 | 5 | 0 | 0 |
|  | 10 | 5 | 5 | 5 | 5 | 0 | 0 |
| 30 | 5 | 5 | 5 | 5 | 5 | 0 | 0 |
|  | 10 | 5 | 5 | 5 | 5 | 0 | 0 |
| 32 | 5 | 5 | 5 | 5 | 5 | 0 | 0 |
|  | 10 | 5 | 5 | 5 | 5 | 0 | 0 |
| 36 | 5 | 5 | 5 | 5 | 5 | 0 | 0 |
|  | 10 | 5 | 5 | 5 | 5 | 0 | 0 |
| 37 | 5 | 5 | 5 | 5 | 5 | 0 | 0 |
|  | 10 | 5 | 5 | 5 | 5 | 0 | 0 |
| 39 | 5 | 5 | 5 | 5 | 5 | 0 | 0 |
|  | 10 | 5 | 5 | 5 | 5 | 0 | 0 |
| 42 | 5 | 5 | 5 | 5 | 5 | 0 | 0 |
|  | 10 | 5 | 5 | 5 | 5 | 0 | 0 |
| 43 | 5 | 5 | 5 | 5 | 5 | 0 | 0 |
|  | 10 | 5 | 5 | 5 | 5 | 0 | 0 |
| 44 | 5 | 5 | 5 | 5 | 5 | 0 | 0 |
|  | 10 | 5 | 5 | 5 | 5 | 0 | 0 |
| 45 | 5 | 5 | 5 | 5 | 5 | 0 | 0 |
|  | 10 | 5 | 5 | 5 | 5 | 0 | 0 |
| 47 | 5 | 5 | 5 | 5 | 5 | 0 | 0 |
|  | 10 | 5 | 5 | 5 | 5 | 0 | 0 |
| 51 | 5 | 5 | 5 | 5 | 5 | 0 | 0 |
|  | 10 | 5 | 5 | 5 | 5 | 0 | 0 |
| 52 | 5 | 5 | 5 | 5 | 5 | 0 | 0 |
|  | 10 | 5 | 5 | 5 | 5 | 0 | 0 |
| 53 | 5 | 5 | 5 | 5 | 5 | 0 | 0 |
|  | 10 | 5 | 5 | 5 | 5 | 0 | 0 |
| 54 | 5 | 5 | 5 | 5 | 5 | 0 | 0 |
|  | 10 | 5 | 5 | 5 | 5 | 0 | 0 |
| 55 | 5 | 5 | 5 | 5 | 5 | 0 | 0 |
|  | 10 | 5 | 5 | 5 | 5 | 0 | 0 |
| 56 | 5 | 5 | 5 | 5 | 5 | 0 | 0 |
|  | 10 | 5 | 5 | 5 | 5 | 0 | 0 |
| 57 | 5 | 5 | 5 | 5 | 5 | 0 | 0 |
|  | 10 | 5 | 5 | 5 | 5 | 0 | 0 |
| 71 | 5 | 5 | 5 | 5 | 5 | 0 | 0 |
|  | 10 | 5 | 5 | 5 | 5 | 0 | 0 |
| 72 | 5 | 5 | 5 | 5 | 5 | 0 | 0 |
|  | 10 | 5 | 5 | 5 | 5 | 0 | 0 |
| 73 | 5 | 5 | 5 | 5 | 5 | 0 | 0 |
|  | 10 | 5 | 5 | 5 | 5 | 0 | 0 |

TABLE 3-continued

| Tested compound No. | Amount of active ingredient used, g/a | Weeds | | | | Crops | |
|---|---|---|---|---|---|---|---|
| | | Crab-grass | Barn-yard-grass | Red-root pig-weed | Lambs quart-ers | Soy-bean | Cot-ton |
| 74 | 5 | 5 | 5 | 5 | 5 | 0 | 0 |
| | 10 | 5 | 5 | 5 | 5 | 0 | 0 |
| 75 | 5 | 5 | 5 | 5 | 5 | 0 | 0 |
| | 10 | 5 | 5 | 5 | 5 | 0 | 0 |
| 76 | 5 | 5 | 5 | 5 | 5 | 0 | 0 |
| | 10 | 5 | 5 | 5 | 5 | 0 | 0 |
| 77 | 5 | 5 | 5 | 5 | 5 | 0 | 0 |
| | 10 | 5 | 5 | 5 | 5 | 0 | 0 |
| 78 | 5 | 5 | 5 | 5 | 5 | 0 | 0 |
| | 10 | 5 | 5 | 5 | 5 | 0 | 0 |
| 79 | 5 | 5 | 5 | 5 | 5 | 0 | 0 |
| | 10 | 5 | 5 | 5 | 5 | 0 | 0 |
| 84 | 5 | 5 | 5 | 5 | 5 | 0 | 0 |
| | 10 | 5 | 5 | 5 | 5 | 0 | 0 |
| 87 | 5 | 5 | 5 | 5 | 5 | 0 | 0 |
| | 10 | 5 | 5 | 5 | 5 | 0 | 0 |
| 94 | 5 | 5 | 5 | 5 | 5 | 0 | 0 |
| | 10 | 5 | 5 | 5 | 5 | 0 | 0 |
| 95 | 5 | 5 | 5 | 5 | 5 | 0 | 0 |
| | 10 | 5 | 5 | 5 | 5 | 0 | 0 |
| 108 | 5 | 5 | 5 | 5 | 5 | 0 | 0 |
| | 10 | 5 | 5 | 5 | 5 | 0 | 0 |
| 109 | 5 | 5 | 5 | 5 | 5 | 0 | 0 |
| | 10 | 5 | 5 | 5 | 5 | 0 | 0 |
| 110 | 5 | 5 | 5 | 5 | 5 | 0 | 0 |
| | 10 | 5 | 5 | 5 | 5 | 0 | 0 |
| 118 | 5 | 5 | 5 | 5 | 5 | 0 | 0 |
| | 10 | 5 | 5 | 5 | 5 | 0 | 0 |
| 119 | 5 | 5 | 5 | 5 | 5 | 0 | 0 |
| | 10 | 5 | 5 | 5 | 5 | 0 | 0 |
| 120 | 5 | 5 | 5 | 5 | 5 | 0 | 0 |
| | 10 | 5 | 5 | 5 | 5 | 0 | 0 |
| 121 | 5 | 5 | 5 | 5 | 5 | 0 | 0 |
| | 10 | 5 | 5 | 5 | 5 | 0 | 0 |
| 124 | 5 | 5 | 5 | 5 | 5 | 0 | 0 |
| | 10 | 5 | 5 | 5 | 5 | 0 | 0 |
| 125 | 5 | 5 | 5 | 5 | 5 | 0 | 0 |
| | 10 | 5 | 5 | 5 | 5 | 0 | 0 |
| 129 | 5 | 5 | 5 | 5 | 5 | 0 | 0 |
| | 10 | 5 | 5 | 5 | 5 | 0 | 0 |
| 131 | 5 | 5 | 5 | 5 | 5 | 0 | 0 |
| | 10 | 5 | 5 | 5 | 5 | 0 | 0 |
| 134 | 5 | 5 | 5 | 5 | 5 | 0 | 0 |
| | 10 | 5 | 5 | 5 | 5 | 0 | 0 |
| 135 | 5 | 5 | 5 | 5 | 5 | 0 | 0 |
| | 10 | 5 | 5 | 5 | 5 | 0 | 0 |
| 143 | 5 | 5 | 5 | 5 | 5 | 0 | 0 |
| | 10 | 5 | 5 | 5 | 5 | 0 | 0 |
| 144 | 5 | 5 | 5 | 5 | 5 | 0 | 0 |
| | 10 | 5 | 5 | 5 | 5 | 0 | 0 |
| 145 | 5 | 5 | 5 | 5 | 5 | 0 | 0 |
| | 10 | 5 | 5 | 5 | 5 | 0 | 0 |
| 146 | 5 | 5 | 5 | 5 | 5 | 0 | 0 |
| | 10 | 5 | 5 | 5 | 5 | 0 | 0 |
| 148 | 5 | 5 | 5 | 5 | 5 | 0 | 0 |
| | 10 | 5 | 5 | 5 | 5 | 0 | 0 |
| 149 | 5 | 5 | 5 | 5 | 5 | 0 | 0 |
| | 10 | 5 | 5 | 5 | 5 | 0 | 0 |
| 150 | 5 | 5 | 5 | 5 | 5 | 0 | 0 |
| | 10 | 5 | 5 | 5 | 5 | 0 | 0 |
| 155 | 5 | 5 | 5 | 5 | 5 | 0 | 0 |
| | 10 | 5 | 5 | 5 | 5 | 0 | 0 |
| 156 | 5 | 5 | 5 | 5 | 5 | 0 | 0 |
| | 10 | 5 | 5 | 5 | 5 | 0 | 0 |
| 157 | 5 | 5 | 5 | 5 | 5 | 0 | 0 |
| | 10 | 5 | 5 | 5 | 5 | 0 | 0 |
| 158 | 5 | 5 | 5 | 5 | 5 | 0 | 0 |
| | 10 | 5 | 5 | 5 | 5 | 0 | 0 |
| 159 | 5 | 5 | 5 | 5 | 5 | 0 | 0 |
| | 10 | 5 | 5 | 5 | 5 | 0 | 0 |
| 160 | 5 | 5 | 5 | 5 | 5 | 0 | 0 |
| | 10 | 5 | 5 | 5 | 5 | 0 | 0 |
| 161 | 5 | 5 | 5 | 5 | 5 | 0 | 0 |
| | 10 | 5 | 5 | 5 | 5 | 0 | 0 |
| 165 | 5 | 5 | 5 | 5 | 5 | 0 | 0 |
| | 10 | 5 | 5 | 5 | 5 | 0 | 0 |
| 166 | 5 | 5 | 5 | 5 | 5 | 0 | 0 |
| | 10 | 5 | 5 | 5 | 5 | 0 | 0 |
| 167 | 5 | 5 | 5 | 5 | 5 | 0 | 0 |
| | 10 | 5 | 5 | 5 | 5 | 0 | 0 |
| 168 | 5 | 5 | 5 | 5 | 5 | 0 | 0 |
| | 10 | 5 | 5 | 5 | 5 | 0 | 0 |
| 169 | 5 | 5 | 5 | 5 | 5 | 0 | 0 |
| | 10 | 5 | 5 | 5 | 5 | 0 | 0 |
| 170 | 5 | 5 | 5 | 5 | 5 | 0 | 0 |
| | 10 | 5 | 5 | 5 | 5 | 0 | 0 |
| 171 | 5 | 5 | 5 | 5 | 5 | 0 | 0 |
| | 10 | 5 | 5 | 5 | 5 | 0 | 0 |
| 172 | 5 | 5 | 5 | 5 | 5 | 0 | 0 |
| | 10 | 5 | 5 | 5 | 5 | 0 | 0 |
| 177 | 5 | 5 | 5 | 5 | 5 | 0 | 0 |
| | 10 | 5 | 5 | 5 | 5 | 0 | 0 |
| 183 | 5 | 5 | 5 | 5 | 5 | 0 | 0 |
| | 10 | 5 | 5 | 5 | 5 | 0 | 0 |
| 186 | 5 | 5 | 5 | 5 | 4 | 0 | 0 |
| | 10 | 5 | 5 | 5 | 5 | 0 | 0 |
| 189 | 5 | 5 | 5 | 5 | 5 | 0 | 0 |
| | 10 | 5 | 5 | 5 | 5 | 0 | 0 |
| 191 | 5 | 5 | 5 | 4 | 4 | 0 | 0 |
| | 10 | 5 | 5 | 5 | 5 | 0 | 0 |
| 193 | 5 | 5 | 5 | 5 | 5 | 0 | 0 |
| | 10 | 5 | 5 | 5 | 5 | 0 | 0 |
| 196 | 5 | 5 | 5 | 5 | 5 | 0 | 0 |
| | 10 | 5 | 5 | 5 | 5 | 0 | 0 |
| 198 | 5 | 5 | 5 | 5 | 5 | 0 | 0 |
| | 10 | 5 | 5 | 5 | 5 | 0 | 0 |
| 199 | 5 | 5 | 5 | 5 | 5 | 0 | 0 |
| | 10 | 5 | 5 | 5 | 5 | 0 | 0 |
| 200 | 5 | 5 | 5 | 5 | 5 | 0 | 0 |
| | 10 | 5 | 5 | 5 | 5 | 0 | 0 |
| 202 | 5 | 5 | 5 | 5 | 5 | 0 | 0 |
| | 10 | 5 | 5 | 5 | 5 | 0 | 0 |
| 205 | 5 | 5 | 5 | 5 | 4 | 0 | 0 |
| | 10 | 5 | 5 | 5 | 5 | 0 | 0 |
| Commercial product NIP* | 20 | 5 | 4 | 4 | 4 | 0 | 0 |
| | 40 | 5 | 5 | 5 | 5 | 0 | 0 |
| Untreated section | Number of plants. | 43 | 38 | 28 | 19 | 5 | 5 |
| | Air dried weight of plants (g) | 2.8 | 4.1 | 2.4 | 2.8 | 10.3 | 6.4 |

*Active ingredient: 2,4-dichloro-4'-nitrodiphenyl ether

TEST EXAMPLE 2

Herbicidal test for treating stems and leaves of dry field crops.

An air-dried soil of dry field (passed through a 14 mesh sieve) (450 g) was placed in a pot made of a resin (a/10000), and a compound fertilizer (N, $P_2O_5$ and $K_2O$, each 100 mg) was applied to the whole layer of the soil, followed by adjusting the water content of the soil to 60% of the maximum water-holding capacity. The soil was seeded with a fixed amount of seeds of a plant to be tested, and uniformly covered with soil. The resulting pot was placed in a glass-covered greenhouse, and when the plant to be tested grew till the period in 2-3 leaves, treatment of stems and leaves was carried out employing a wettable powder prepared according to the above-mentioned Formulation example 4, so as to contain the agent to be tested, in an amount of 1000, 2000 or 5000 ppm in terms of active ingredient.

Thirty days after the treatment, the growth condition of the plant to be tested was investigated to obtain the results shown in Table 4. In addition, in this Table, the designated sections of the growth condition of the crops and weeds are the same as those of Table 3.

Among the compounds shown in Table 4, compounds Nos. 5, 9, 26, 61, 62, 63, 70, 175, 179, 186, 190 and 197 could completely control the following weeds, in an amount of agent used, of 5 g/a, and other compounds could control them in an amount of agent used, of 2 g/a:

Foxtail, Bluegrass, Foxtailgrass, Johnsongrass, Bermudagrass, Quackgrass, Smartweed, Velvetleaf, Morningglory, Hertleaf cocklebur, *Rumex japonicus*, Wild mustard, Shepherdspurse, etc.

TABLE 4

| Tested compound No. | Amount of active ingredient used, g/a | Weeds | | | Crops | |
|---|---|---|---|---|---|---|
| | | Crabgrass | Barnyardgrass | Redroot pigweed | Lambsquarters | Soybean | Cotton |
| 5 | 2 | 5 | 5 | 4 | 5 | 0 | 0 |
|   | 5 | 5 | 5 | 5 | 5 | 0 | 0 |
| 9 | 2 | 5 | 5 | 4 | 5 | 0 | 0 |
|   | 5 | 5 | 5 | 5 | 5 | 0 | 0 |
| 12 | 2 | 5 | 5 | 5 | 4 | 0 | 0 |
|    | 5 | 5 | 5 | 5 | 5 | 0 | 0 |
| 15 | 2 | 5 | 5 | 5 | 5 | 0 | 0 |
|    | 5 | 5 | 5 | 5 | 5 | 0 | 0 |
| 17 | 2 | 5 | 5 | 5 | 5 | 0 | 0 |
|    | 5 | 5 | 5 | 5 | 5 | 0 | 0 |
| 18 | 2 | 5 | 5 | 5 | 5 | 0 | 0 |
|    | 5 | 5 | 5 | 5 | 5 | 0 | 0 |
| 23 | 2 | 5 | 5 | 5 | 5 | 0 | 0 |
|    | 5 | 5 | 5 | 5 | 5 | 0 | 0 |
| 26 | 2 | 5 | 5 | 4 | 4 | 0 | 0 |
|    | 5 | 5 | 5 | 5 | 5 | 0 | 0 |
| 27 | 2 | 5 | 5 | 5 | 5 | 0 | 0 |
|    | 5 | 5 | 5 | 5 | 5 | 0 | 0 |
| 31 | 2 | 5 | 5 | 5 | 5 | 0 | 0 |
|    | 5 | 5 | 5 | 5 | 5 | 0 | 0 |
| 44 | 2 | 5 | 5 | 5 | 5 | 0 | 0 |
|    | 5 | 5 | 5 | 5 | 5 | 0 | 0 |
| 45 | 2 | 5 | 5 | 5 | 5 | 0 | 0 |
|    | 5 | 5 | 5 | 5 | 5 | 0 | 0 |
| 59 | 2 | 5 | 5 | 4 | 5 | 0 | 0 |
|    | 5 | 5 | 5 | 5 | 5 | 0 | 0 |
| 61 | 2 | 5 | 5 | 4 | 5 | 0 | 0 |
|    | 5 | 5 | 5 | 5 | 5 | 0 | 0 |
| 62 | 2 | 5 | 5 | 4 | 5 | 0 | 0 |
|    | 5 | 5 | 5 | 5 | 5 | 0 | 0 |
| 63 | 2 | 5 | 5 | 4 | 5 | 0 | 0 |
|    | 5 | 5 | 5 | 5 | 5 | 0 | 0 |
| 64 | 2 | 5 | 5 | 4 | 5 | 0 | 0 |
|    | 5 | 5 | 5 | 5 | 5 | 0 | 0 |
| 66 | 2 | 5 | 5 | 5 | 4 | 0 | 0 |
|    | 5 | 5 | 5 | 5 | 5 | 0 | 0 |
| 67 | 2 | 5 | 5 | 5 | 4 | 0 | 0 |
|    | 5 | 5 | 5 | 5 | 5 | 0 | 0 |
| 69 | 2 | 5 | 5 | 5 | 4 | 0 | 0 |
|    | 5 | 5 | 5 | 5 | 5 | 0 | 0 |
| 70 | 2 | 5 | 5 | 5 | 4 | 0 | 0 |
|    | 5 | 5 | 5 | 5 | 5 | 0 | 0 |
| 71 | 2 | 5 | 5 | 5 | 5 | 0 | 0 |
|    | 5 | 5 | 5 | 5 | 5 | 0 | 0 |
| 73 | 2 | 5 | 5 | 5 | 5 | 0 | 0 |
|    | 5 | 5 | 5 | 5 | 5 | 0 | 0 |
| 74 | 2 | 5 | 5 | 5 | 5 | 0 | 0 |
|    | 5 | 5 | 5 | 5 | 5 | 0 | 0 |
| 76 | 2 | 5 | 5 | 5 | 5 | 0 | 0 |
|    | 5 | 5 | 5 | 5 | 5 | 0 | 0 |
| 77 | 2 | 5 | 5 | 5 | 5 | 0 | 0 |
|    | 5 | 5 | 5 | 5 | 5 | 0 | 0 |
| 84 | 2 | 5 | 5 | 5 | 5 | 0 | 0 |
|    | 5 | 5 | 5 | 5 | 5 | 0 | 0 |
| 94 | 2 | 5 | 5 | 5 | 5 | 0 | 0 |
|    | 5 | 5 | 5 | 5 | 5 | 0 | 0 |
| 95 | 2 | 5 | 5 | 5 | 5 | 0 | 0 |

TABLE 4-continued

| Tested compound No. | Amount of active ingredient used, g/a | Weeds | | | | Crops | |
|---|---|---|---|---|---|---|---|
| | | Crabgrass | Barnyardgrass | Redroot pigweed | Lambsquarters | Soybean | Cotton |
| | | 5 | 5 | 5 | 5 | 0 | 0 |
| 97 | 2 | 5 | 5 | 5 | 5 | 0 | 0 |
|    | 5 | 5 | 5 | 5 | 5 | 0 | 0 |
| 98 | 2 | 5 | 5 | 5 | 5 | 0 | 0 |
|    | 5 | 5 | 5 | 5 | 5 | 0 | 0 |
| 99 | 2 | 5 | 5 | 5 | 5 | 0 | 0 |
|    | 5 | 5 | 5 | 5 | 5 | 0 | 0 |
| 100 | 2 | 5 | 5 | 5 | 5 | 0 | 0 |
|     | 5 | 5 | 5 | 5 | 5 | 0 | 0 |
| 101 | 2 | 5 | 5 | 5 | 5 | 0 | 0 |
|     | 5 | 5 | 5 | 5 | 5 | 0 | 0 |
| 118 | 2 | 5 | 5 | 5 | 5 | 0 | 0 |
|     | 5 | 5 | 5 | 5 | 5 | 0 | 0 |
| 119 | 2 | 5 | 5 | 5 | 5 | 0 | 0 |
|     | 5 | 5 | 5 | 5 | 5 | 0 | 0 |
| 123 | 2 | 5 | 5 | 5 | 5 | 0 | 0 |
|     | 5 | 5 | 5 | 5 | 5 | 0 | 0 |
| 132 | 2 | 5 | 5 | 5 | 5 | 0 | 0 |
|     | 5 | 5 | 5 | 5 | 5 | 0 | 0 |
| 133 | 2 | 5 | 5 | 5 | 5 | 0 | 0 |
|     | 5 | 5 | 5 | 5 | 5 | 0 | 0 |
| 137 | 2 | 5 | 5 | 5 | 5 | 0 | 0 |
|     | 5 | 5 | 5 | 5 | 5 | 0 | 0 |
| 140 | 2 | 5 | 5 | 5 | 5 | 0 | 0 |
|     | 5 | 5 | 5 | 5 | 5 | 0 | 0 |
| 142 | 2 | 5 | 5 | 5 | 5 | 0 | 0 |
|     | 5 | 5 | 5 | 5 | 5 | 0 | 0 |
| 169 | 2 | 5 | 5 | 5 | 5 | 0 | 0 |
|     | 5 | 5 | 5 | 5 | 5 | 0 | 0 |
| 173 | 2 | 5 | 5 | 5 | 5 | 0 | 0 |
|     | 5 | 5 | 5 | 5 | 5 | 0 | 0 |
| 174 | 2 | 5 | 5 | 5 | 5 | 0 | 0 |
|     | 5 | 5 | 5 | 5 | 5 | 0 | 0 |
| 175 | 2 | 5 | 5 | 4 | 4 | 0 | 0 |
|     | 5 | 5 | 5 | 5 | 5 | 0 | 0 |
| 176 | 2 | 5 | 5 | 5 | 5 | 0 | 0 |
|     | 5 | 5 | 5 | 5 | 5 | 0 | 0 |
| 179 | 2 | 5 | 4 | 4 | 4 | 0 | 0 |
|     | 5 | 5 | 5 | 5 | 5 | 0 | 0 |
| 182 | 2 | 5 | 5 | 5 | 5 | 0 | 0 |
|     | 5 | 5 | 5 | 5 | 5 | 0 | 0 |
| 185 | 2 | 5 | 5 | 5 | 5 | 0 | 0 |
|     | 5 | 5 | 5 | 5 | 5 | 0 | 0 |
| 186 | 2 | 5 | 4 | 5 | 5 | 0 | 0 |
|     | 5 | 5 | 5 | 5 | 5 | 0 | 0 |
| 187 | 2 | 5 | 5 | 5 | 5 | 0 | 0 |
|     | 5 | 5 | 5 | 5 | 5 | 0 | 0 |
| 188 | 2 | 5 | 5 | 5 | 5 | 0 | 0 |
|     | 5 | 5 | 5 | 5 | 5 | 0 | 0 |
| 190 | 2 | 5 | 5 | 5 | 5 | 0 | 0 |
|     | 5 | 5 | 5 | 5 | 5 | 0 | 0 |
| 192 | 2 | 5 | 5 | 5 | 5 | 0 | 0 |
|     | 5 | 5 | 5 | 5 | 5 | 0 | 0 |
| 194 | 2 | 5 | 5 | 5 | 5 | 0 | 0 |
|     | 5 | 5 | 5 | 5 | 5 | 0 | 0 |
| 195 | 2 | 5 | 4 | 5 | 5 | 0 | 0 |
|     | 5 | 5 | 5 | 5 | 5 | 0 | 0 |
| 197 | 2 | 5 | 5 | 5 | 5 | 0 | 0 |
|     | 5 | 5 | 5 | 5 | 5 | 0 | 0 |
| 201 | 2 | 5 | 5 | 5 | 4 | 0 | 0 |
|     | 5 | 5 | 5 | 5 | 5 | 0 | 0 |
| 202 | 2 | 5 | 5 | 5 | 5 | 0 | 0 |
|     | 5 | 5 | 5 | 5 | 5 | 0 | 0 |
| 206 | 2 | 5 | 5 | 5 | 4 | 0 | 0 |
|     | 5 | 5 | 5 | 5 | 5 | 0 | 0 |
| 207 | 2 | 5 | 5 | 5 | 5 | 0 | 0 |
|     | 5 | 5 | 5 | 5 | 5 | 0 | 0 |
| 208 | 2 | 5 | 5 | 5 | 5 | 0 | 0 |
|     | 5 | 5 | 5 | 5 | 5 | 0 | 0 |
| Commercial product NIP | 10 | 4 | 4 | 4 | 4 | 2 | 2 |
| | 20 | 5 | 5 | 5 | 5 | 3 | 3 |
| Un- | Number of | 10 | 10 | 10 | 10 | 5 | 5 |

TABLE 4-continued

| Tested compound No. | Amount of active ingredient used, g/a | Weeds | | | | Crops | |
|---|---|---|---|---|---|---|---|
| | | Crab-grass | Barn-yard grass | Red-root pig-weed | Lambs quart-ers | Soy-bean | Cot-ton |
| treated section | plants Air-dried weight of plants (g) | 22.5 | 31.8 | 30.9 | 29.3 | 3.3 | 7.1 |

TEST EXAMPLE 3

Herbicidal test for initial period paddy field (1).

A paddy field soil wherein seeds of general weeds of paddy field were naturally present in admixture (passed through a 14 mesh sieve) (3.3 Kg) was placed in a Wagner pot (a/5000), and a compound fertilizer (N, $P_2O_5$ and $K_2O$, each 0.8 g) was applied to the whole layer of the soil, followed by adding a proper amount of water and stirring to form a water-filled state. The soil was seeded with seeds of weeds of paddy field and tubers of *Sagittaria trifolia* and *Eleocharis kuroguwai*, and two stocks, each consisting of two young aquatic rice plants (leaf age of young plant: 3.0), grown in advance, were transplanted to grow them in a greenhouse.

At the initial period of occurrence of weeds two days after the transplantation of the aquatic rice plants, treatment was carried out under the water-filled condition, employing granules prepared from a fixed amount of compounds to be tested, according to the above-mentioned Formulation example 5.

One month after the treatment, the occurrence condition of weeds and the extent of phytotoxicity upon the aquatic rice plants were investigated to obtain the results shown in Table 5. In this Table, the sections designating the occurrence condition of weeds were made 6 stages as in Test example 1, and the sections designating the extent of phytotoxicity upon aquatic rice plants were made 6 stage of "serious harm", "large harm", "medium harm", "small harm", "slight harm" and "non-harm".

In addition, during the test period, the water-filled depth of the pot was maintained at 3 cm, by way of a water-leakage treatment of 1 cm/day.

Among the tested compounds shown in Table 5, compounds Nos. 1, 2, 4, 6, 48, 93, 103, 191 and 192 could control Eleocharis kuroguwai and Sagittaria trifola in an amount of agent used, of 15 g/a, and other compounds could control them in an amount of agent used, of 7 g/a.

Evaluation standards upon phytotoxicity:

| Serious harm: | Percentage of existence of crops indicated by the air-dried weight ratio relative to crops in untreated section | 0–10% |
| Large harm: | Percentage of existence of crops indicated by the air-dried weight ratio relative to crops in untreated section | 11–20% |
| Medium harm: | Percentage of existence of crops indicated by the air-dried weight ratio relative to crops in untreated section | 21–50% |
| Small harm: | Percentage of existence of crops indicated by the air-dried weight ratio relative to crops in untreated section | 51–80% |
| Slight harm: | Percentage of existence of crops indicated by the air-dried weight ratio relative to crops in untreated section | 81–95% |
| Non-harm: | Percentage of existence of crops indicated by the air-dried weight ratio relative to crops in untreated section | 96–100% |

TABLE 5

| Tested compound No. | Amount of active ingredient used, g/a | Weeds | | | | | Crops Aquatic rice |
|---|---|---|---|---|---|---|---|
| | | Barn-yard-grass | Small-flower umbrella-plant | *Scirpus juncoides* | Narrow-leaf water-plantain | Annual broad leaf | |
| 1 | 5 | 4 | 5 | 5 | 5 | 5 | Non |
| | 10 | 5 | 5 | 5 | 5 | 5 | " |
| 2 | 5 | 4 | 5 | 5 | 5 | 5 | Non |
| | 10 | 5 | 5 | 5 | 5 | 5 | " |
| 3 | 5 | 4 | 5 | 5 | 5 | 5 | Non |
| | 10 | 5 | 5 | 5 | 5 | 5 | " |
| 4 | 5 | 4 | 5 | 5 | 5 | 5 | Non |
| | 10 | 5 | 5 | 5 | 5 | 5 | " |
| 6 | 5 | 4 | 5 | 5 | 5 | 5 | Non |
| | 10 | 5 | 5 | 5 | 5 | 5 | " |
| 8 | 5 | 5 | 5 | 5 | 5 | 5 | Non |
| | 10 | 5 | 5 | 5 | 5 | 5 | " |
| 18 | 5 | 5 | 5 | 5 | 5 | 5 | Non |
| | 10 | 5 | 5 | 5 | 5 | 5 | " |
| 23 | 5 | 5 | 5 | 5 | 5 | 5 | Non |
| | 10 | 5 | 5 | 5 | 5 | 5 | " |
| 28 | 5 | 5 | 5 | 5 | 5 | 5 | Non |
| | 10 | 5 | 5 | 5 | 5 | 5 | " |
| 34 | 5 | 5 | 5 | 5 | 5 | 5 | Non |
| | 10 | 5 | 5 | 5 | 5 | 5 | " |
| 35 | 5 | 4 | 5 | 5 | 5 | 5 | Non |
| | 10 | 5 | 5 | 5 | 5 | 5 | " |
| 44 | 5 | 5 | 5 | 5 | 5 | 5 | Non |
| | 10 | 5 | 5 | 5 | 5 | 5 | " |
| 48 | 5 | 4 | 5 | 5 | 5 | 5 | Non |
| | 10 | 5 | 5 | 5 | 5 | 5 | " |
| 49 | 5 | 5 | 5 | 5 | 5 | 5 | Non |
| | 10 | 5 | 5 | 5 | 5 | 5 | " |
| 50 | 5 | 4 | 5 | 5 | 5 | 5 | Non |
| | 10 | 5 | 5 | 5 | 5 | 5 | " |

TABLE 5-continued

| Tested compound No. | Amount of active ingredient used, g/a | Weeds | | | | | Crops Aquatic rice |
|---|---|---|---|---|---|---|---|
| | | Barn-yard-grass | Small-flower umbrella-plant | Scirpus juncoides | Narrow-leaf water-plantain | Annual broad leaf | |
| 51 | 5 | 5 | 5 | 5 | 5 | 5 | Non |
| | 10 | 5 | 5 | 5 | 5 | 5 | " |
| 58 | 5 | 5 | 5 | 5 | 5 | 5 | Non |
| | 10 | 5 | 5 | 5 | 5 | 5 | " |
| 65 | 5 | 4 | 5 | 5 | 5 | 5 | Non |
| | 10 | 5 | 5 | 5 | 5 | 5 | " |
| 76 | 5 | 5 | 5 | 5 | 5 | 5 | Non |
| | 10 | 5 | 5 | 5 | 5 | 5 | " |
| 77 | 5 | 5 | 5 | 5 | 5 | 5 | Non |
| | 10 | 5 | 5 | 5 | 5 | 5 | " |
| 78 | 5 | 5 | 5 | 5 | 5 | 5 | Non |
| | 10 | 5 | 5 | 5 | 5 | 5 | " |
| 79 | 5 | 5 | 5 | 5 | 5 | 5 | Non |
| | 10 | 5 | 5 | 5 | 5 | 5 | " |
| 80 | 5 | 4 | 5 | 5 | 5 | 5 | Non |
| | 10 | 5 | 5 | 5 | 5 | 5 | " |
| 81 | 5 | 5 | 5 | 5 | 5 | 5 | Non |
| | 10 | 5 | 5 | 5 | 5 | 5 | " |
| 82 | 5 | 4 | 5 | 5 | 5 | 5 | Non |
| | 10 | 5 | 5 | 5 | 5 | 5 | " |
| 83 | 5 | 5 | 5 | 5 | 5 | 5 | Non |
| | 10 | 5 | 5 | 5 | 5 | 5 | " |
| 84 | 5 | 5 | 5 | 5 | 5 | 5 | Non |
| | 10 | 5 | 5 | 5 | 5 | 5 | " |
| 85 | 5 | 5 | 5 | 5 | 5 | 5 | Non |
| | 10 | 5 | 5 | 5 | 5 | 5 | " |
| 86 | 5 | 4 | 5 | 5 | 5 | 5 | Non |
| | 10 | 5 | 5 | 5 | 5 | 5 | " |
| 88 | 5 | 4 | 5 | 5 | 5 | 5 | Non |
| | 10 | 5 | 5 | 5 | 5 | 5 | " |
| 89 | 5 | 5 | 5 | 5 | 5 | 5 | Non |
| | 10 | 5 | 5 | 5 | 5 | 5 | " |
| 90 | 5 | 4 | 5 | 5 | 5 | 5 | Non |
| | 10 | 5 | 5 | 5 | 5 | 5 | " |
| 91 | 5 | 5 | 5 | 5 | 5 | 5 | Non |
| | 10 | 5 | 5 | 5 | 5 | 5 | " |
| 92 | 5 | 4 | 5 | 5 | 5 | 5 | Non |
| | 10 | 5 | 5 | 5 | 5 | 5 | " |
| 93 | 5 | 4 | 5 | 5 | 5 | 5 | Non |
| | 10 | 5 | 5 | 5 | 5 | 5 | " |
| 94 | 5 | 5 | 5 | 5 | 5 | 5 | Non |
| | 10 | 5 | 5 | 5 | 5 | 5 | " |
| 95 | 5 | 5 | 5 | 5 | 5 | 5 | Non |
| | 10 | 5 | 5 | 5 | 5 | 5 | " |
| 96 | 5 | 5 | 5 | 5 | 5 | 5 | Non |
| | 10 | 5 | 5 | 5 | 5 | 5 | " |
| 97 | 5 | 5 | 5 | 5 | 5 | 5 | Non |
| | 10 | 5 | 5 | 5 | 5 | 5 | " |
| 98 | 5 | 5 | 5 | 5 | 5 | 5 | Non |
| | 10 | 5 | 5 | 5 | 5 | 5 | " |
| 99 | 5 | 5 | 5 | 5 | 5 | 5 | Non |
| | 10 | 5 | 5 | 5 | 5 | 5 | " |
| 101 | 5 | 5 | 5 | 5 | 5 | 5 | Non |
| | 10 | 5 | 5 | 5 | 5 | 5 | " |
| 102 | 5 | 5 | 5 | 5 | 5 | 5 | Non |
| | 10 | 5 | 5 | 5 | 5 | 5 | " |
| 103 | 5 | 4 | 5 | 5 | 5 | 5 | Non |
| | 10 | 5 | 5 | 5 | 5 | 5 | " |
| 104 | 5 | 4 | 5 | 5 | 5 | 5 | Non |
| | 10 | 5 | 5 | 5 | 5 | 5 | " |
| 105 | 5 | 4 | 5 | 5 | 5 | 5 | Non |
| | 10 | 5 | 5 | 5 | 5 | 5 | " |
| 106 | 5 | 5 | 5 | 5 | 5 | 5 | Non |
| | 10 | 5 | 5 | 5 | 5 | 5 | " |
| 107 | 5 | 4 | 5 | 5 | 5 | 5 | Non |
| | 10 | 5 | 5 | 5 | 5 | 5 | " |
| 109 | 5 | 5 | 5 | 5 | 5 | 5 | Non |
| | 10 | 5 | 5 | 5 | 5 | 5 | " |
| 123 | 5 | 4 | 5 | 5 | 5 | 5 | Non |
| | 10 | 5 | 5 | 5 | 5 | 5 | " |
| 134 | 5 | 5 | 5 | 5 | 5 | 5 | Non |
| | 10 | 5 | 5 | 5 | 5 | 5 | " |
| 142 | 5 | 5 | 5 | 5 | 5 | 5 | Non |
| | 10 | 5 | 5 | 5 | 5 | 5 | " |
| 147 | 5 | 5 | 5 | 5 | 5 | 5 | Non |
| | 10 | 5 | 5 | 5 | 5 | 5 | " |
| 151 | 5 | 5 | 5 | 5 | 5 | 5 | Non |

TABLE 5-continued

| Tested compound No. | Amount of active ingredient used, g/a | Weeds | | | | | Crops Aquatic rice |
|---|---|---|---|---|---|---|---|
| | | Barn-yard-grass | Small-flower umbrella-plant | *Scirpus juncoides* | Narrow-leaf water-plantain | Annual broad leaf | |
| | 10 | 5 | 5 | 5 | 5 | 5 | " |
| 152 | 5 | 5 | 5 | 5 | 5 | 5 | Non |
| | 10 | 5 | 5 | 5 | 5 | 5 | " |
| 153 | 5 | 5 | 5 | 5 | 5 | 5 | Non |
| | 10 | 5 | 5 | 5 | 5 | 5 | " |
| 154 | 5 | 5 | 5 | 5 | 5 | 5 | Non |
| | 10 | 5 | 5 | 5 | 5 | 5 | " |
| 162 | 5 | 5 | 5 | 5 | 5 | 5 | Non |
| | 10 | 5 | 5 | 5 | 5 | 5 | " |
| 163 | 5 | 5 | 5 | 5 | 5 | 5 | Non |
| | 10 | 5 | 5 | 5 | 5 | 5 | " |
| 164 | 5 | 5 | 5 | 5 | 5 | 5 | Non |
| | 10 | 5 | 5 | 5 | 5 | 5 | " |
| 165 | 5 | 5 | 5 | 5 | 5 | 5 | Non |
| | 10 | 5 | 5 | 5 | 5 | 5 | " |
| 166 | 5 | 5 | 5 | 5 | 5 | 5 | Non |
| | 10 | 5 | 5 | 5 | 5 | 5 | " |
| 173 | 5 | 5 | 5 | 5 | 5 | 5 | Non |
| | 10 | 5 | 5 | 5 | 5 | 5 | " |
| 174 | 5 | 5 | 5 | 5 | 5 | 5 | Non |
| | 10 | 5 | 5 | 5 | 5 | 5 | " |
| 175 | 5 | 5 | 5 | 5 | 5 | 5 | Non |
| | 10 | 5 | 5 | 5 | 5 | 5 | " |
| 176 | 5 | 5 | 5 | 5 | 5 | 5 | Non |
| | 10 | 5 | 5 | 5 | 5 | 5 | " |
| 177 | 5 | 5 | 5 | 5 | 5 | 5 | Non |
| | 10 | 5 | 5 | 5 | 5 | 5 | " |
| 178 | 5 | 5 | 5 | 5 | 5 | 5 | Non |
| | 10 | 5 | 5 | 5 | 5 | 5 | " |
| 179 | 5 | 5 | 5 | 5 | 5 | 5 | Non |
| | 10 | 5 | 5 | 5 | 5 | 5 | " |
| 180 | 5 | 5 | 5 | 5 | 5 | 5 | Non |
| | 10 | 5 | 5 | 5 | 5 | 5 | " |
| 181 | 5 | 5 | 5 | 5 | 5 | 5 | Non |
| | 10 | 5 | 5 | 5 | 5 | 5 | " |
| 182 | 5 | 5 | 5 | 5 | 5 | 5 | Non |
| | 10 | 5 | 5 | 5 | 5 | 5 | " |
| 183 | 5 | 5 | 5 | 5 | 5 | 5 | Non |
| | 10 | 5 | 5 | 5 | 5 | 5 | " |
| 184 | 5 | 5 | 5 | 5 | 5 | 5 | Non |
| | 10 | 5 | 5 | 5 | 5 | 5 | " |
| 186 | 5 | 5 | 5 | 5 | 5 | 5 | Non |
| | 10 | 5 | 5 | 5 | 5 | 5 | " |
| 187 | 5 | 5 | 5 | 5 | 5 | 5 | Non |
| | 10 | 5 | 5 | 5 | 5 | 5 | " |
| 188 | 5 | 5 | 4 | 5 | 4 | 4 | Non |
| | 10 | 5 | 5 | 5 | 5 | 5 | " |
| 189 | 5 | 5 | 4 | 4 | 4 | 5 | Non |
| | 10 | 5 | 5 | 5 | 5 | 5 | " |
| 190 | 5 | 5 | 4 | 4 | 5 | 5 | Non |
| | 10 | 5 | 5 | 5 | 5 | 5 | " |
| 191 | 5 | 5 | 5 | 5 | 5 | 5 | Non |
| | 10 | 5 | 5 | 5 | 5 | 5 | " |
| 192 | 5 | 5 | 5 | 5 | 5 | 5 | Non |
| | 10 | 5 | 5 | 5 | 5 | 5 | " |
| 193 | 5 | 5 | 5 | 5 | 5 | 5 | Non |
| | 10 | 5 | 5 | 5 | 5 | 5 | " |
| 194 | 5 | 5 | 5 | 5 | 5 | 5 | Non |
| | 10 | 5 | 5 | 5 | 5 | 5 | " |
| 195 | 5 | 5 | 5 | 5 | 5 | 5 | Non |
| | 10 | 5 | 5 | 5 | 5 | 5 | " |
| 196 | 5 | 5 | 5 | 5 | 5 | 5 | Non |
| | 10 | 5 | 5 | 5 | 5 | 5 | " |
| 197 | 5 | 5 | 5 | 5 | 5 | 5 | Non |
| | 10 | 5 | 5 | 5 | 5 | 5 | " |
| 201 | 5 | 5 | 5 | 4 | 5 | 5 | Non |
| | 10 | 5 | 5 | 5 | 5 | 5 | " |
| 203 | 5 | 5 | 5 | 5 | 5 | 5 | Non |
| | 10 | 5 | 5 | 5 | 5 | 5 | " |
| 204 | 5 | 5 | 5 | 5 | 5 | 5 | Non |
| | 10 | 5 | 5 | 5 | 5 | 5 | " |
| 207 | 5 | 5 | 5 | 5 | 5 | 5 | Non |
| | 10 | 5 | 5 | 5 | 5 | 5 | " |
| 208 | 5 | 5 | 5 | 5 | 5 | 5 | Non |
| | 10 | 5 | 5 | 5 | 5 | 5 | " |
| Com-mercial | 20 | 5 | 5 | 4 | 4 | 5 | Non |
| | 40 | 5 | 5 | 5 | 5 | 5 | Slight |

TABLE 5-continued

| Tested compound No. | Amount of active ingredient used, g/a | Weeds | | | | | Crops Aquatic rice |
|---|---|---|---|---|---|---|---|
| | | Barn-yard-grass | Small-flower umbrella-plant | *Scirpus juncoides* | Narrow-leaf water-plantain | Annual broad leaf | |
| product X52* | | | | | | | |
| Un-treated section | Number of plants | 114 | 38 | 43 | 62 | 76 | 4 |
| | Air-dried weight of plants (g) | 9.1 | 0.12 | 1.81 | 0.23 | 0.14 | 21.1 |

*Active ingredient: 2,4-dichloro-3'-methoxy-4'-nitrodiphenyl ether

TEST EXAMPLE 4

Herbicidal test for initial period paddy field (2).

A paddy field soil wherein seeds of general weeds of paddy field were naturally present in admixture (passed through a 14 mesh sieve) (3.3 Kg) was placed in a Wagner pot (a/5000), and a compound fertilizer (N, $P_2O_5$ and $K_2O$, each 0.8 g) was applied to the whole layer of the soil, followed by adding water and stirring to form a water-filled state. The soil was seeded with seeds of weeds of paddy field and tubers of Sagittaria trifolia and Eleocharis kuroguwai, and two stocks, each consisting of two yound aquatic rice plants (leaf age of young plant: 3.0), grown in advance, were transplanted to grow them in a greenhouse.

At the initial period of occurrence of weeds seven days after the transplantation of the aquatic rice plant, treatment was carried out under the water-filled condition, employing granules prepared from a fixed amount of compounds to be tested, according to the above-mentioned Formulation example 1.

One month after the treatment, the occurrence condition of weeds and the extent of phytotoxicity upon the aquatic rice plants were investigated to obtain the results shown in Table 6. In this Table, the sections designating the occurrence condition of weeds were made 6 stages as in Test example 1, and the sections designating the extent of phytotoxicity upon aquatic rice plants were made 6 stages of "serious harm", "large harm", "medium harm", "small harm", "slight harm" and "non-harm". The evaluation standards are the same as those in Test example 3.

In addition, during the test period, the water-filled depth of the pot was maintained at 3 cm, by way of a water-leakage treatment of 1 cm/day.

Among the tested compounds shown in Table 6, compounds Nos. 10, 33, 68, 112, 126, 127, 132, 165, 174, 176, 186, 187, 195 and 197 could control *Sagittaria trifola* and *Eleocharis kuroguwai* in an amount of agent used, of 20 g/a, and other compounds could control them in an amount of agent used, of 15 g/a.

TABLE 6

| Tested compound No. | Amount of active ingredient used, g/a | Weeds | | | | | Crops Aquatic rice |
|---|---|---|---|---|---|---|---|
| | | Barn-yard-grass | Small-flower umbrella-plant | *Scirpus juncoides* | Narrow leaf water-plantain | Annual broad leaf | |
| 10 | 7 | 4 | 5 | 5 | 5 | 5 | Non |
| | 15 | 5 | 5 | 5 | 5 | 5 | " |
| 14 | 7 | 4 | 5 | 5 | 5 | 5 | Non |
| | 15 | 5 | 5 | 5 | 5 | 5 | " |
| 20 | 7 | 5 | 5 | 5 | 5 | 5 | Non |
| | 15 | 5 | 5 | 5 | 5 | 5 | " |
| 33 | 7 | 4 | 5 | 5 | 5 | 5 | Non |
| | 15 | 5 | 5 | 5 | 5 | 5 | " |
| 40 | 7 | 5 | 5 | 5 | 5 | 5 | Non |
| | 15 | 5 | 5 | 5 | 5 | 5 | " |
| 41 | 7 | 5 | 5 | 5 | 5 | 5 | Non |
| | 15 | 5 | 5 | 5 | 5 | 5 | " |
| 42 | 7 | 5 | 5 | 5 | 5 | 5 | Non |
| | 15 | 5 | 5 | 5 | 5 | 5 | " |
| 43 | 7 | 5 | 5 | 5 | 5 | 5 | Non |
| | 15 | 5 | 5 | 5 | 5 | 5 | " |
| 45 | 7 | 5 | 5 | 5 | 5 | 5 | Non |
| | 15 | 5 | 5 | 5 | 5 | 5 | " |
| 46 | 7 | 5 | 5 | 5 | 5 | 5 | Non |
| | 15 | 5 | 5 | 5 | 5 | 5 | " |
| 68 | 7 | 4 | 5 | 5 | 5 | 5 | Non |
| | 15 | 5 | 5 | 5 | 5 | 5 | " |
| 74 | 7 | 5 | 5 | 5 | 5 | 5 | Non |
| | 15 | 5 | 5 | 5 | 5 | 5 | " |
| 75 | 7 | 5 | 5 | 5 | 5 | 5 | Non |
| | 15 | 5 | 5 | 5 | 5 | 5 | " |
| 76 | 7 | 5 | 5 | 5 | 5 | 5 | Non |
| | 15 | 5 | 5 | 5 | 5 | 5 | " |
| 77 | 7 | 5 | 5 | 5 | 5 | 5 | Non |
| | 15 | 5 | 5 | 5 | 5 | 5 | " |
| 83 | 7 | 5 | 5 | 5 | 5 | 5 | Non |
| | 15 | 5 | 5 | 5 | 5 | 5 | " |
| 87 | 7 | 5 | 5 | 5 | 5 | 5 | Non |

TABLE 6-continued

| Tested compound No. | Amount of active ingredient used, g/a | Weeds | | | | | Crops Aquatic rice |
|---|---|---|---|---|---|---|---|
| | | Barn-yard-grass | Small-flower umbrella-plant | *Scirpus juncoides* | Narrow leaf water-plantain | Annual broad leaf | |
| | 15 | 5 | 5 | 5 | 5 | 5 | " |
| 97 | 7 | 5 | 5 | 5 | 5 | 5 | Non |
| | 15 | 5 | 5 | 5 | 5 | 5 | " |
| 100 | 7 | 5 | 5 | 5 | 5 | 5 | Non |
| | 15 | 5 | 5 | 5 | 5 | 5 | " |
| 111 | 7 | 4 | 5 | 5 | 5 | 5 | Non |
| | 15 | 5 | 5 | 5 | 5 | 5 | " |
| 112 | 7 | 4 | 5 | 5 | 5 | 5 | Non |
| | 15 | 5 | 5 | 5 | 5 | 5 | " |
| 113 | 7 | 5 | 5 | 5 | 5 | 5 | Non |
| | 15 | 5 | 5 | 5 | 5 | 5 | " |
| 114 | 7 | 5 | 5 | 5 | 5 | 5 | Non |
| | 15 | 5 | 5 | 5 | 5 | 5 | " |
| 115 | 7 | 5 | 5 | 5 | 5 | 5 | Non |
| | 15 | 5 | 5 | 5 | 5 | 5 | " |
| 116 | 7 | 5 | 5 | 5 | 5 | 5 | Non |
| | 15 | 5 | 5 | 5 | 5 | 5 | " |
| 117 | 7 | 5 | 5 | 5 | 5 | 5 | Non |
| | 15 | 5 | 5 | 5 | 5 | 5 | " |
| 120 | 7 | 5 | 5 | 5 | 5 | 5 | Non |
| | 15 | 5 | 5 | 5 | 5 | 5 | " |
| 122 | 7 | 5 | 5 | 5 | 5 | 5 | Non |
| | 15 | 5 | 5 | 5 | 5 | 5 | " |
| 126 | 7 | 4 | 5 | 5 | 5 | 5 | Non |
| | 15 | 5 | 5 | 5 | 5 | 5 | " |
| 127 | 7 | 4 | 5 | 5 | 5 | 5 | Non |
| | 15 | 5 | 5 | 5 | 5 | 5 | " |
| 128 | 7 | 4 | 5 | 5 | 5 | 5 | Non |
| | 15 | 5 | 5 | 5 | 5 | 5 | " |
| 129 | 7 | 5 | 5 | 5 | 5 | 5 | Non |
| | 15 | 5 | 5 | 5 | 5 | 5 | " |
| 130 | 7 | 4 | 5 | 5 | 5 | 5 | Non |
| | 15 | 5 | 5 | 5 | 5 | 5 | " |
| 131 | 7 | 5 | 5 | 5 | 5 | 5 | Non |
| | 15 | 5 | 5 | 5 | 5 | 5 | " |
| 132 | 7 | 4 | 5 | 5 | 5 | 5 | Non |
| | 15 | 5 | 5 | 5 | 5 | 5 | " |
| 135 | 7 | 5 | 5 | 5 | 5 | 5 | Non |
| | 15 | 5 | 5 | 5 | 5 | 5 | " |
| 138 | 7 | 5 | 5 | 5 | 5 | 5 | Non |
| | 15 | 5 | 5 | 5 | 5 | 5 | " |
| 139 | 7 | 4 | 5 | 5 | 5 | 5 | Non |
| | 15 | 5 | 5 | 5 | 5 | 5 | " |
| 141 | 7 | 4 | 5 | 5 | 5 | 5 | Non |
| | 15 | 5 | 5 | 5 | 5 | 5 | " |
| 142 | 7 | 5 | 5 | 5 | 5 | 5 | Non |
| | 15 | 5 | 5 | 5 | 5 | 5 | " |
| 143 | 7 | 5 | 5 | 5 | 5 | 5 | Non |
| | 15 | 5 | 5 | 5 | 5 | 5 | " |
| 165 | 7 | 5 | 5 | 5 | 5 | 5 | Non |
| | 15 | 5 | 5 | 5 | 5 | 5 | " |
| 166 | 7 | 5 | 5 | 5 | 5 | 5 | Non |
| | 15 | 5 | 5 | 5 | 5 | 5 | " |
| 174 | 7 | 5 | 5 | 5 | 5 | 5 | Non |
| | 15 | 5 | 5 | 5 | 5 | 5 | " |
| 176 | 7 | 5 | 5 | 5 | 5 | 5 | Non |
| | 15 | 5 | 5 | 5 | 5 | 5 | " |
| 180 | 7 | 5 | 5 | 5 | 5 | 5 | Non |
| | 15 | 5 | 5 | 5 | 5 | 5 | " |
| 184 | 7 | 5 | 5 | 5 | 5 | 5 | Non |
| | 15 | 5 | 5 | 5 | 5 | 5 | " |
| 185 | 7 | 5 | 5 | 5 | 5 | 5 | Non |
| | 15 | 5 | 5 | 5 | 5 | 5 | " |
| 186 | 7 | 5 | 5 | 5 | 5 | 5 | Non |
| | 15 | 5 | 5 | 5 | 5 | 5 | " |
| 187 | 7 | 5 | 5 | 5 | 5 | 5 | Non |
| | 15 | 5 | 5 | 5 | 5 | 5 | " |
| 188 | 7 | 5 | 5 | 4 | 5 | 5 | Non |
| | 15 | 5 | 5 | 5 | 5 | 5 | " |
| 189 | 7 | 5 | 5 | 5 | 5 | 5 | Non |
| | 15 | 5 | 5 | 5 | 5 | 5 | " |
| 192 | 7 | 5 | 5 | 5 | 5 | 5 | Non |
| | 15 | 5 | 5 | 5 | 5 | 5 | " |
| 193 | 7 | 5 | 5 | 5 | 5 | 5 | Non |
| | 15 | 5 | 5 | 5 | 5 | 5 | " |
| 195 | 7 | 5 | 5 | 5 | 5 | 5 | Non |
| | 15 | 5 | 5 | 5 | 5 | 5 | " |

TABLE 6-continued

| Tested compound No. | Amount of active ingredient used, g/a | Weeds | | | | | Crops Aquatic rice |
|---|---|---|---|---|---|---|---|
| | | Barn-yard-grass | Small-flower umbrella-plant | *Scirpus juncoides* | Narrow leaf water-plantain | Annual broad leaf | |
| 197 | 7 | 5 | 5 | 5 | 5 | 5 | Non |
|  | 15 | 5 | 5 | 5 | 5 | 5 | " |
| 203 | 7 | 5 | 5 | 5 | 5 | 5 | Non |
|  | 15 | 5 | 5 | 5 | 5 | 5 | " |
| 204 | 7 | 5 | 5 | 5 | 5 | 5 | Non |
|  | 15 | 5 | 5 | 5 | 5 | 5 | " |
| 206 | 7 | 5 | 5 | 4 | 5 | 5 | Non |
|  | 15 | 5 | 5 | 5 | 5 | 5 | " |
| 207 | 7 | 5 | 5 | 5 | 5 | 5 | Non |
|  | 15 | 5 | 5 | 5 | 5 | 5 | " |
| 208 | 7 | 5 | 5 | 5 | 5 | 5 | Non |
|  | 15 | 5 | 5 | 5 | 5 | 5 | " |
| Commercial product Attack Weed* | 40 | 4 | 4 | 2 | 4 | 4 | Slight |
|  | 60 | 5 | 5 | 3 | 4 | 5 | Non |
| Untreated section | Number of plants | 93 | 28 | 38 | 75 | 45 | 4 |
|  | Air-dried weight of plants (g) | 49.1 | 0.11 | 0.29 | 0.38 | 0.21 | 59.2 |

*Active ingredient: 3-methyl-4-nitrodiphenyl ether

What is claimed is:

1. A diphenyl ether compound represented by the general formula I,

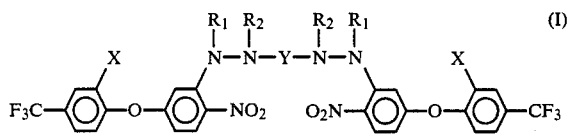

wherein X is hydrogen or chlorine atom, $R_1$ and $R_2$ each stands for hydrogen or a lower alkyl group and Y is —CO—, —COCO— or —CO(CH$_2$)$_n$CO— wherein n is an integer of from 1 to 4.

2. A compound of claim 1 represented by the general formula I wherein X is a chlorine atom.

3. A herbicidal composition containing as an active ingredient a herbicidally effective amount of a diphenyl ether compound of claim 1 and also containing an inert herbicidal carrier.

4. A herbicidal composition containing as an active ingredient a herbicidally effective amount of a diphenyl ether compound of claim 2 and also containing an inert herbicidal carrier.

5. A method of controlling weeds which comprises applying a herbicidally effective amount of a compound of claim 1 pre-emergently to the soil.

6. A method of controlling weeds which comprises applying a herbicidally effective amount of a compound of claim 2 pre-emergently to the soil.

7. A method of controlling weeds which comprises applying a herbicidally effective amount of a compound of claim 1 post-emergently to the weeds.

8. A method of controlling weeds which comprises applying a herbicidally effective amount of a compound of claim 2 post-emergently to the weeds.

* * * * *